(12) United States Patent
Badylak et al.

(10) Patent No.: US 11,389,569 B2
(45) Date of Patent: Jul. 19, 2022

(54) BIODEGRADABLE, POROUS, THERMALLY RESPONSIVE INJECTABLE HYDROGEL AS SOFT TISSUE DEFECT FILLER

(71) Applicant: University of Pittsburgh—Of the Commonwealth System of Higher Education, Pittsburgh, PA (US)

(72) Inventors: Stephen F. Badylak, West Lafayette, IN (US); Hong Jiang, Export, PA (US); Hideyoshi Sato, Pittsburgh, PA (US); William R. Wagner, Gibsonia, PA (US); Yang Zhu, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 20 days.

(21) Appl. No.: 16/496,480

(22) PCT Filed: Apr. 3, 2018

(86) PCT No.: PCT/US2018/025829
§ 371 (c)(1),
(2) Date: Sep. 23, 2019

(87) PCT Pub. No.: WO2018/187286
PCT Pub. Date: Oct. 11, 2018

(65) Prior Publication Data
US 2020/0030495 A1    Jan. 30, 2020

Related U.S. Application Data

(60) Provisional application No. 62/480,820, filed on Apr. 3, 2017.

(51) Int. Cl.
| | | |
|---|---|---|
| A61L 27/56 | (2006.01) | |
| A61L 27/26 | (2006.01) | |
| A61L 27/48 | (2006.01) | |
| A61L 27/52 | (2006.01) | |
| C08L 33/24 | (2006.01) | |

(52) U.S. Cl.
CPC ............... *A61L 27/56* (2013.01); *A61L 27/26* (2013.01); *A61L 27/48* (2013.01); *A61L 27/52* (2013.01); *C08L 33/24* (2013.01)

(58) Field of Classification Search
None
See application file for complete search history.

(56) References Cited

U.S. PATENT DOCUMENTS

| | | |
|---|---|---|
| 4,902,508 A | 2/1990 | Badylak et al. |
| 4,956,178 A | 9/1990 | Badylak et al. |
| 5,281,422 A | 1/1994 | Badylak et al. |
| 5,352,463 A | 10/1994 | Badylak et al. |
| 5,372,821 A | 12/1994 | Badylak et al. |
| 5,554,389 A | 9/1996 | Badylak et al. |
| 5,573,784 A | 11/1996 | Badylak et al. |
| 5,645,860 A | 7/1997 | Knapp, Jr. et al. |
| 5,753,267 A | 5/1998 | Badylak et al. |
| 5,762,966 A | 6/1998 | Knapp, Jr. et al. |
| 5,771,969 A | 6/1998 | Garay |
| 5,866,414 A | 2/1999 | Badylak et al. |
| 6,099,567 A | 8/2000 | Badylak et al. |
| 6,485,723 B1 | 11/2002 | Badylak et al. |
| 6,576,265 B1 | 6/2003 | Spievack |
| 6,579,538 B1 | 6/2003 | Spievack |
| 6,696,270 B2 | 2/2004 | Badylak et al. |
| 6,783,776 B2 | 8/2004 | Spievack |
| 6,793,939 B2 | 9/2004 | Badylak |
| 6,849,273 B2 | 2/2005 | Spievack |
| 6,852,339 B2 | 2/2005 | Spievack |
| 6,861,074 B2 | 3/2005 | Spievack |
| 6,887,495 B2 | 5/2005 | Spievack |
| 6,890,562 B2 | 5/2005 | Spievack |
| 6,890,563 B2 | 5/2005 | Spievack |
| 6,890,564 B2 | 5/2005 | Spievack |
| 6,893,666 B2 | 5/2005 | Spievack |
| 8,361,503 B2 | 1/2013 | Badylak et al. |
| 8,461,132 B2 | 6/2013 | Cohen et al. |
| 8,673,295 B2 | 3/2014 | Fujimoto et al. |
| 8,691,276 B2 | 4/2014 | Badylak et al. |

(Continued)

FOREIGN PATENT DOCUMENTS

| | | |
|---|---|---|
| CA | 2723118 C | 11/2009 |
| CN | 101574514 A | 11/2009 |

(Continued)

OTHER PUBLICATIONS

Hong et al. "Tailoring the degradation kinetics of poly(ester-carbonate urethane)urea thermoplastic elastomers for tissue engineering scaffolds", Biomaterials, 31(15): 4249-4258, 2010.

Huleihel et al. "Matrix-bound nanovesicles within ECM bioscaffolds", Science Advances, 2(6): e1600502, 2016.

Ma et al. "A thermally responsive injectable hydrogel incorporating methacrylate-polylactide for hydrolytic lability", Biomacromolecules, 11(7): 1873-1881, 2010.

Nelson et al. "Intramyocardial biomaterial injection therapy in the treatment of heart failure: Materials, outcomes and challenges", Acta Biomater, 7(1): 1-15, 2011.

Seif-Naraghi et al. "Safety and efficacy of an injectable extracellular matrix hydrogel for treating myocardial infarction", Sci Transl Med, 5(173), 2013.

(Continued)

*Primary Examiner* — Robert A Wax
*Assistant Examiner* — Randeep Singh
(74) *Attorney, Agent, or Firm* — The Webb Law Firm

(57) ABSTRACT

An injectable hydrogel composition that forms a porous gel rapidly after injection fro tissue engineering. The composition comprises a biodegradable, biocompatible, gelling polymer, that is optionally reverse-gelling; an Extra cellular matrix (ECM) material and a biocompatible porogen. Methods of making and using the composition are provided. A kit also is provided comprising the ingredients for making the hydrogel.

14 Claims, 11 Drawing Sheets

(56) References Cited

U.S. PATENT DOCUMENTS

| | | | |
|---|---|---|---|
| 8,889,791 B2 | 11/2014 | Guan et al. | |
| 9,408,855 B2 | 8/2016 | Fujimoto et al. | |
| 2007/0178159 A1* | 8/2007 | Chen | A61L 27/54 424/484 |
| 2009/0022817 A1 | 1/2009 | Michal et al. | |
| 2011/0117195 A1 | 5/2011 | Hsieh et al. | |
| 2011/0142787 A1 | 6/2011 | Nagasaki et al. | |
| 2013/0156862 A1 | 6/2013 | Badylak et al. | |
| 2013/0236513 A1* | 9/2013 | Guelcher | A61K 38/1875 424/400 |
| 2014/0178450 A1* | 6/2014 | Christman | A61K 9/0024 424/422 |
| 2016/0325016 A1 | 11/2016 | Amoroso et al. | |
| 2017/0028101 A1 | 2/2017 | Jiang et al. | |

FOREIGN PATENT DOCUMENTS

| | | |
|---|---|---|
| CN | 101618235 A | 1/2010 |
| EP | 2109469 B1 | 10/2009 |
| WO | 02087481 A1 | 11/2002 |
| WO | 2008045904 A2 | 4/2008 |
| WO | 2010127254 A2 | 11/2010 |
| WO | 2012164101 A1 | 12/2012 |
| WO | 2015143310 A1 | 9/2015 |
| WO | 2015160793 A1 | 10/2015 |
| WO | 2017123883 A1 | 7/2017 |
| WO | 2017223529 A1 | 12/2017 |

OTHER PUBLICATIONS

Tous et al. "Injectable Acellular Hydrogels for Cardiac Repair", Journal of Cardiovascular Translational Research, 4:528-542, 2011.

Vo et al. "Injectable dual-gelling cell-laden composite hydrogels for bone tissue engineering", Biomaterials, 83: 1-11, 2016.

Zhu et al. "Design of a coupled thermoresponsive hydrogel and robotic system for postinfarct biomaterial injection therapy", The Annals of Thoracic Surgery, 102(3): 780-786, 2016.

* cited by examiner

BIODEGRADABLE, POROUS, THERMALLY RESPONSIVE INJECTABLE HYDROGEL AS SOFT TISSUE DEFECT FILLER

CROSS REFERENCE TO RELATED APPLICATIONS

This application is the United States national phase of International Application No. PCT/US2018/025829 filed Apr. 3, 2018, and claims the benefit of U.S. Provisional Patent Application No. 62/480,820 filed Apr. 3, 2017, the disclosure of each of which is incorporated herein by reference in its entirety.

STATEMENT REGARDING FEDERAL FUNDING

This invention was made with government support under Grant No. HL105911 awarded by the National Institutes of Health. The government has certain rights in the invention.

Provided herein are injectable, porous soft tissue fillers. Methods of making and using the injectable, porous soft tissue fillers also are provided.

Biodegradable injectable hydrogels have found extensive applications in tissue engineering and a variety of medical procedures, including providing local tissue mechanical support and as vehicles for drug and cell delivery in soft tissue repair. One of the advantages of injectable hydrogels is that they can be delivered minimally invasively in a designed, controllable manner. In addition, the biodegradability of injectable hydrogels allows tissue regrowth and remodeling. Although injectable hydrogels exist that solidify in vivo after injection, there is a need to develop a method to fabricate porous, injectable hydrogels that rapidly solidify upon injection.

SUMMARY

According to one aspect of the invention, a composition is provided. The composition comprises: a biodegradable, biocompatible, gelling polymer composition, that is optionally reverse-gelling; ECM material; and a biocompatible porogen that dissolves in vivo within 48 hours, or optionally within 24 hours, and wherein the composition forms a gel at 37° C. within one hour, 30 minutes, 15 minutes, five minutes, or two minutes.

According to another aspect of the invention, a method of making a composition for use in tissue repair is provided. the method comprises: mixing a biodegradable, biocompatible, gelling polymer composition, that is optionally reverse gelling, with a comminuted or solubilized ECM material, and a biocompatible porogen that dissolves in vivo within 48 hours, or optionally 24 hours, wherein the composition forms a gel at 37° C. within one hour, 30 minutes, 15 minutes, five minutes, or two minutes, wherein the composition optionally forms a gel at in vivo within ten minutes, five minutes, or two minutes, and optionally wherein the porogen particles have a size or average size of between 30 µm and 300 µm.

According to a further aspect of the invention, a method of treating a defect or wound in a patient, comprising administering to the patient at or adjacent to the site of the wound or defect in the patient, an amount of the composition described above effective to treat or repair the wound or defect in a patient, wherein the defect or wound optionally is a soft tissue defect or wound.

According to yet another aspect of the invention, a kit is provided. The kit comprises one or more vessels containing: a biodegradable, biocompatible, gelling polymer composition that is optionally reverse-gelling; comminuted or solubilized ECM material; and a biocompatible porogen that dissolves in vivo within 48 hours, or optionally 24 hours, wherein the polymer composition, the comminuted or solubilized ECM material, and the porogen are contained together or in separate vessels in a liquid, frozen, dried, or lyophilized state.

BRIEF DESCRIPTION OF THE DRAWINGS

FIG. 5A. (panel a) DAPI staining of rat hindlimb muscle 3 days after hydrogel injection, scale bar=500 µm. FIG. 5B. Trichrome staining of rat hindlimb muscle 3 days after hydrogel injection. FIG. 5C. DAPI staining of rat hindlimb muscle 21 days after hydrogel injection. FIG. 5D. Trichrome staining of rat hindlimb muscle 21 days after hydrogel injection. FIGS. 5E and 5F. Relative cell density (muscle=100%) in injected hydrogel and foreign body capsule 3 days and 21 days after injection.

FIG. 6A. CD86 (green in original) and CD68 (red in original) staining. FIG. 6B. CD206 (green in original) and CD68 (red in original) staining. FIG. 6C. CD86 (green in original) and CD68 (red in original) and FIG. 6D. CD206 (green in original) and CD68 (red in original) staining at the hydrogel/muscle interface. FIGS. 6E and 6F. Percentage of $CD86^+$ and $CD206^+$ cells in $CD68^+$ population, respectively. FIG. 6G. Ratio between $CD86^+$ and $CD206^+$ cells in $CD68^+$ population. *Significant difference, $p<0.05$.

FIG. 7A. CD86 (green in original) and CD68 (red in original) staining. FIG. 7B. CD206 (green in original) and CD68 (red in original) staining.

Oil Red staining. (c) Isolectin (red in original)/BIOPSY (green in original)/DAPI staining.

Figure 11A:
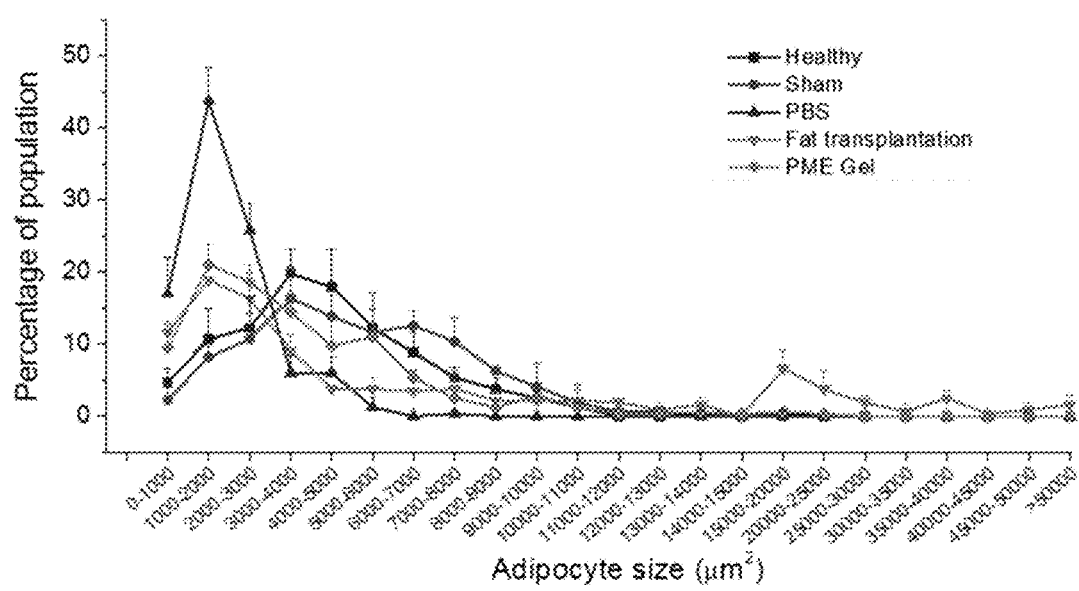
Figure 11B:
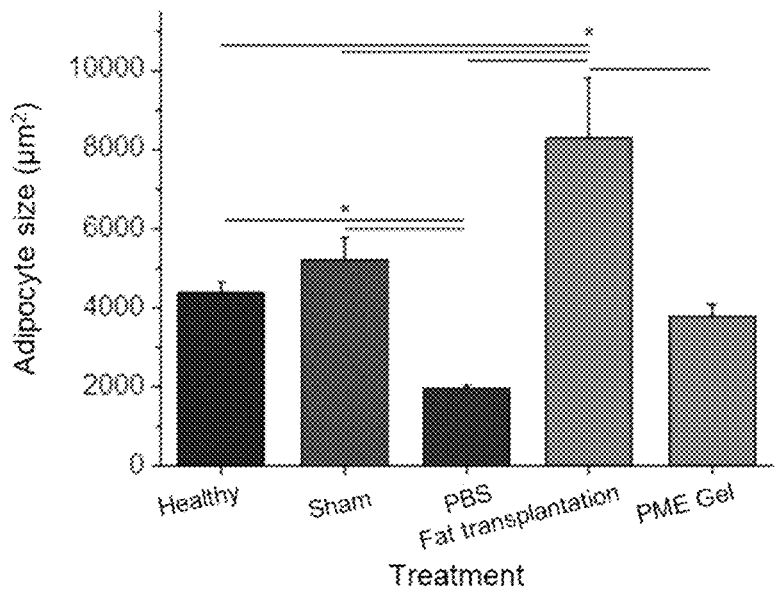
Figure 11C:
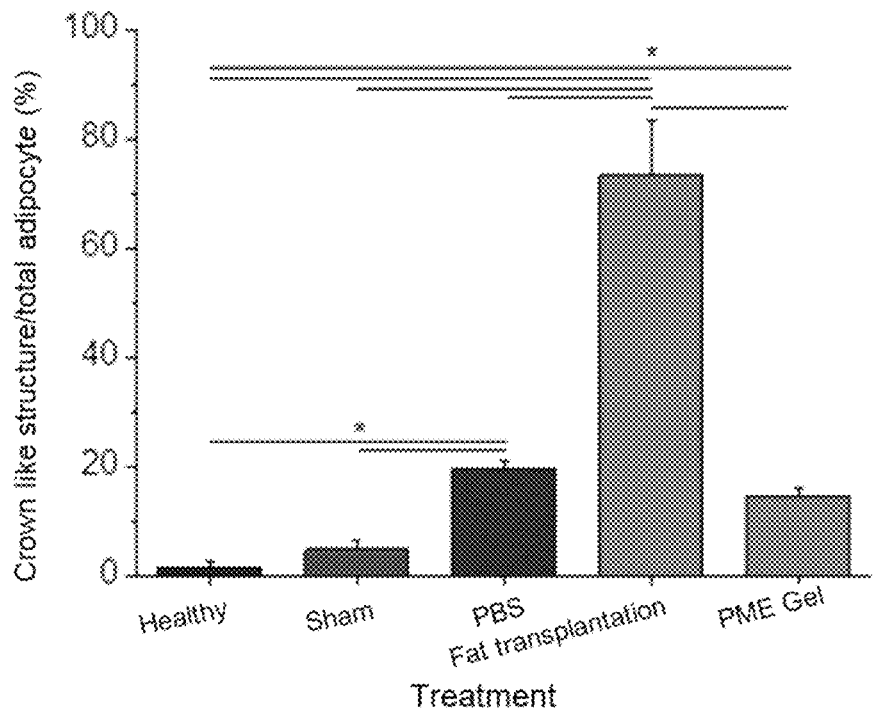

FIGS. 11A-11C. Morphology analysis by adipocyte size and crown-like structure number. FIG. 11A. Frequency distribution of adipocyte size. FIG. 11B. Adipocyte size comparison among treatments. FIG. 11C. Ratio between the quantity of crown-like structure and adipocytes. *Significant difference, $p<0.05$.

DETAILED DESCRIPTION

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. As used herein "a" and "an" refer to one or more.

As used herein, the singular form of "a", "an", and "the" include plural referents unless the context clearly dictates otherwise.

As used herein, the terms "upper", "lower", "right", "left", "vertical", "horizontal", "top", "bottom", "lateral", "longitudinal", and derivatives thereof, shall relate to the invention as it is oriented in the drawing figures. The term "proximal" refers to a portion of a structure nearest to the center of the structure or to a point of attachment or actuation of the structure. For example, a "proximal portion" of a syringe is the portion of the syringe configured to be grasped by a user. The term "distal" refers to a portion of a structure farthest away from the center or from the point of attachment or actuation of the structure (e.g., the portion of the structure opposite from the proximal portion). For example, a "distal portion" of a syringe is the end of the syringe including the needle or nozzle. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Reference to color in certain drawings is with respect to the original, color photographs, which are presented in grayscale herein.

As used herein, the "treatment" or "treating" of a condition, wound, or defect means administration to a patient by any suitable dosage regimen, procedure and/or administration route of a composition, device or structure with the object of achieving a desirable clinical/medical end-point, including repair and/or replacement of a tricuspid or mitral valve.

As used herein, the term "patient" or "subject" refers to members of the animal kingdom including but not limited to human beings and "mammal" refers to all mammals, including, but not limited to human beings.

As used herein, "soft tissue" refers to tissues that connect, support or surround other structures and organs in the body, including, without limitation: fat, muscle, fibrous tissue (tendons and ligaments), synovial tissue (in joints), blood vessels, lymph vessels, and peripheral nerves. The materials described herein can be used as a filler to repair or replace missing or damaged soft tissue, for example and without limitation, as a filler for use in cosmetic and restorative surgery, such as breast reconstruction or facial reconstruction, and in other suitable applications. The materials also can be used to produce compression, movement, and/or displacement of tissue as a therapy.

A polymer composition is "biocompatible" in that the polymer and, where applicable, degradation products thereof, are substantially non-toxic to cells or organisms within acceptable tolerances, including substantially non-carcinogenic and substantially non-immunogenic, and are cleared or otherwise degraded in a biological system, such as an organism (patient) without substantial toxic effect. Non-limiting examples of degradation mechanisms within a biological system include chemical reactions, hydrolysis reactions, and enzymatic cleavage.

As used herein, the term "polymer composition" is a composition comprising one or more polymers. As a class, "polymers" includes, without limitation, homopolymers, heteropolymers, co-polymers, block polymers, block co-polymers and can be both natural and/or synthetic. Homopolymers contain one type of building block, or monomer, whereas copolymers contain more than one type of monomer. The term "(co)polymer" and like terms refer to either homopolymers or copolymers.

A polymer "comprises" or is "derived from" a stated monomer if that monomer is incorporated into the polymer. Thus, the incorporated monomer (monomer residue) that the polymer comprises is not the same as the monomer prior to incorporation into a polymer, in that at the very least, certain groups/moieties are missing and/or modified when incorporated into the polymer backbone. A polymer is said to comprise a specific type of linkage if that linkage is present in the polymer.

As used herein, "reverse gelling" means a composition is a solution at a temperature below 25° C., e.g. 22° C., 20° C., or 15° C., and forms a hydrogel at 37° C. "Shear-thinning" refers to non-Newtonian fluids that lose viscosity under shear strain, such as a stirring force, or forces encountered in a medical syringe when the plunger is moved, and that rapidly regain viscosity in the absence of shear strain.

As described herein, a "fiber" is an elongated, slender, thread-like and/or filamentous structure. A "matrix" is any two- or three-dimensional arrangement of a composition, e.g., a porous structure that optionally comprises elements (e.g., fibers), either ordered (e.g., in a woven or non-woven mesh) or randomly-arranged (as is typical with a mat of fibers typically produced by electrospinning). and can be isotropic or anisotropic. As indicated herein, a porous matrix is a matrix comprising a plurality of pores or interstices, such as a porous hydrogel comprising pores created by the dissolution of a porogen from a solid hydrogel, or openings between fibers deposited in a woven or non-woven mesh.

By "biodegradable or "bioerodable", it is meant that a polymer, once implanted and placed in contact with bodily fluids and tissues, will degrade either partially or completely through chemical reactions with the bodily fluids and/or tissues, typically and often preferably over a time period of hours, days, weeks or months. Non-limiting examples of such chemical reactions include acid/base reactions, hydrolysis reactions, and enzymatic cleavage. The biodegradation rate of the polymer matrix may be manipulated, optimized or otherwise adjusted so that the matrix degrades over a useful time period. The polymer or polymers typically will be selected so that it degrades in situ over a time period to optimize tissue regeneration in its use.

As used herein, the terms "therapeutic agent" and "therapeutic agents" refer to any composition(s), such as drug(s) or active agent(s) having a preventative or therapeutic effect, including and without limitation, antibiotics, peptides, hormones, organic molecules, vitamins, supplements, factors, proteins and chemoattractants. A "therapy" or "treatment" refers to administration of a therapeutic composition, such as the compositions described herein, in amounts effective to reach an acceptable end point, e.g., a clinical end point, such as the filling of, or repair of a soft tissue defect or damage.

As used herein, the terms "cell" and "cells" refer to any types of cells from any animal, such as, without limitation, rat, mice, monkey, and human. For example and without limitation, cells can be progenitor cells, such as stem cells, or differentiated cells, such as endothelial cells, smooth muscle cells. In certain embodiments, cells for medical procedures can be obtained from the patient for autologous procedures or from other donors for allogeneic procedures.

As used herein, the term "porosity" refers to a ratio between a volume of all the pores within the polymer composition and a volume of the whole polymer composition. For instance, a polymer composition with a porosity of 85% would have 85% of its volume containing pores and 15% of its volume containing the polymer. In certain non-limiting embodiments, the porosity of the structure, once to porogen dissolves, is at least 60%, 65%, 70%, 75%, 80%, 85%, or 90%, or increments therebetween.

According to one aspect of the invention, a biodegradable, injectable hydrogel composition is provided herein that can be used, for example and without limitation, as soft tissue defect filler, for injection into or around damaged tissue, such as a myocardial infarct, or for displacement, movement, or compression of tissue. The composition comprises a gelling polymer, an ECM material, and a porogen that dissolves after administration of the composition to a patient. The composition optionally comprises one or more therapeutic agents. The gelling polymer is, in aspects, a reverse-gelling polymer that is a solution at a temperature below 37° C., and typically below 25° C., and rapidly forms a solid hydrogel at 37° C. Prior to injection, the composition is held at a temperature below 37° C., e.g., below 25° C., for instance on ice, and upon injection, the composition warms to physiological temperature and solidifies. The porogen is selected so it does not dissolve substantially in the time period prior to injection, and dissolves within 24 or 48 hours of injection and solidification of the gel. Dissolution of the porogen in vivo results in a porous, biodegradable hydrogel structure supportive of cell infiltration and tissue integration. In another aspect, the polymer composition is not reverse gelling, but is injectable and forms a hydrogel after injection. In yet another aspect, the polymer composition is shear-thinning.

According to one example, the polymer is a poly(NIPAAm-co-VP-co-MAPLA) copolymer, e.g., as described herein, the porogen is mannitol, and the ECM material is solubilized ECM material. In another aspect, the composition is a mixture of 15 wt % (unless otherwise indicated, % refers to percent by weight or % wt.) poly(NIPAAm-co-VP-co-MAPLA), 5 mg/mL decellularized porcine bladder product (ECM) and 10 wt % mannitol particles. The hydrogel is a viscous liquid at low temperature, and can be injected with a syringe into soft tissue defects at 4° C. Upon contact with tissue, the hydrogel solidifies in 15 sec due to a hydrophilic-hydrophobic transition and forms a hydrogel. The mannitol particles subsequently dissolve and leave porous structures in the solidified hydrogel. In various aspects of the invention, the solidified hydrogel may be selected to possess an elastic modulus close to, or higher than soft tissues. Therefore, as a filler, the hydrogel can maintain the geometry of the implantation site. The rapidly-forming porous structure in the hydrogel allows for fast cell infiltration and tissue integration. The ECM component mediates, at least in part, the biological responses to promote healing. For example, in the above-described example, mannitol particles are water soluble and are quickly removed after injection, and MAPLA sidechains in the copolymer are gradually hydrolyzed, at which time the polymer turns hydrophilic and is safely absorbed by tissue. The ECM component in the hydrogel is degraded over time by native enzymes in the tissue.

In one aspect, the ECM composition is comminuted, and optionally protease-solubilized ECM material, such as acid-protease-solubilized material. In another aspect, the ECM composition is a reverse-gelling acid protease- (e.g., pepsin-) digested ECM material that is digested in an acidic solution of, e.g., between pH 1-4, or 1.5-2.5, e.g., 2.0, or in 0.01N HCl, e.g., UBM ECM matrix. In one aspect, the ECM material is not dialyzed prior to acid protease digestion, and in another aspect, the ECM material is not chemically crosslinked, e.g., with glutaraldehyde. In use, as described further below, the composition is injected as an injectable solution, and upon warming to physiological temperature (37° C. for humans), the composition forms a gel and the porogen dissolves, e.g., within 1, 6, 12, 24, or 48 hours, to leave a porous matrix of the polymer and ECM material. The relative amounts of the polymer composition, ECM composition, and porogen can vary—so long as the composition can form a gel upon injection into a patient and warming to physiological temperature. Thus, the amount of ECM material and porogen cannot prevent gelation of the polymer component, and result in a matrix that cannot be maintained in vivo for a time long enough for cells to infiltrate.

In another aspect, a method of making the composition is provided, comprising mixing a gelling biodegradable, biocompatible polymer composition with an ECM composition, and a porogen, and optionally one or more therapeutic agents. The composition forms a gel when injected into a patient. Where the polymer composition is reverse-gelling, the components can be mixed at a temperature at which neither the polymer or the ECM composition forms a gel. The polymer in one aspect is a poly(NIPAAm-co-VP-co-MAPLA) copolymer, e.g., as described herein. The porogen is mannitol in one aspect. In one aspect, the ECM composition is comminuted, and optionally protease-solubilized ECM material, such as acid-protease-solubilized material. In another aspect, the ECM composition is a reverse-gelling acid protease-digested ECM material (e.g., pepsin-digested ECM material) that is digested in an acidic solution of, e.g., between pH 1-4, or 1.5-2.5, e.g., 2.0, or in 0.01N HCl, e.g., UBM ECM matrix. In one aspect, the ECM material is not dialyzed prior to acid protease digestion, and in another aspect, the ECM material is not chemically crosslinked, e.g. with glutaraldehyde. In one aspect, the porogen is added to the polymer and ECM composition immediately prior to use. In one aspect, the polymer composition and ECM material are mixed and are then lyophilized or frozen, such that the porogen is added at a later time, e.g., immediately prior to use. When lyophilized, the composition is re-hydrated, e.g., on ice, prior to use. In another aspect, the polymer composition, ECM composition, and porogen are mixed and are then lyophilized or frozen, and are re-hydrated or thawed, respectively, prior to use, e.g., immediately prior to use, and on ice. In aspects, the polymer composition is shear-thinning. In other aspects, the polymer composition is crosslinked after injection to form a gel. In further aspects, the polymer is shear-thinning and optionally self-healing.

In a further aspect, a method of treating a patient is provided. The method comprises administering a composition to the patient comprising a mixture of a gelling biodegradable, biocompatible polymer composition, an ECM composition, and a porogen, and optionally comprising one or more therapeutic agents. The polymer composition may be cross-linked in situ, shear thinning and optionally self-healing, or reverse gelling. The polymer in one aspect is a poly(NIPAAm-co-VP-co-MAPLA) copolymer, e.g., as described herein. The porogen is mannitol in one aspect. In one aspect, the ECM composition is comminuted, and optionally protease-solubilized ECM material, such as acid-protease-solubilized material. In another aspect, the ECM composition is a reverse-gelling acid protease- (e.g., pepsin-) digested ECM material that is digested in an acidic solution of, e.g., between pH 1-4, or 1.5-2.5, e.g., 2.0, or in 0.01N HCl, e.g., UBM ECM matrix. In one aspect, the ECM material is not dialyzed prior to acid protease digestion, and in another aspect, the ECM material is not chemically crosslinked, e.g., with glutaraldehyde. The composition is injected in the patient as an injectable solution, and upon warming to physiological temperature (37° C. for humans), the composition forms a gel and the porogen dissolves, e.g., within 1, 6, 12, 24, or 48 hours, to leave a porous matrix of the polymer and ECM material. Cells grow within the nascent porous matrix, thereby repairing the injury or defect.

In aspects of the treatment method, the patient may have a wound or defect, or any condition amenable to treatment with the porous gel-forming composition described herein. In one aspect, the composition is administered, for example, to fill a void in a patient that may have been caused by injury/trauma, a congenital condition, an illness, or a surgical procedure, such as resection of a tumor. In another aspect, the composition is administered to produce compression, displacement, movement, of tissue in the patient, to facilitate healing or corrective healing of a condition in the patient.

In yet another aspect, a kit is provided comprising at least one vessel containing a composition comprising a mixture of a gelling biodegradable, biocompatible polymer composition, an acid protease-digested ECM composition, and a porogen, and optionally comprising one or more therapeutic agents. In aspects, the polymer composition may be cross-linked in situ, shear thinning and optionally self-healing, or reverse gelling, for example, as described herein. The polymer, in one non-limiting aspect, is a poly(NIPAAm-co-VP-co-MAPLA) copolymer, e.g., as described herein. The porogen is mannitol in one aspect. In one aspect, the ECM composition is comminuted, and optionally protease-solubilized ECM material, such as acid-protease-solubilized material. In another aspect, the ECM composition is a reverse-gelling acid protease- (e.g., pepsin-) digested ECM material that is digested in an acidic solution of, e.g., between pH 1-4, or 1.5-2.5, e.g., 2.0, or in 0.01N HCl, e.g., UBM ECM matrix. In one aspect, the ECM material is not dialyzed prior to acid protease digestion, and in another aspect, the ECM material is not chemically crosslinked, e.g., with glutaraldehyde. In use, as described further below, the composition comprising the reverse-gelling polymer is injected as an injectable solution, and upon warming to physiological temperature (37° C. for humans), the composition forms a gel and the porogen dissolves, e.g., within 1, 6, 12, 24, or 48 hours, to leave a porous matrix of the polymer and ECM material. The vessel is preferably kept cool, e.g., cooler than 20° C., 15° C., 10° C., 5° C., or even at a temperature at which the composition is frozen. Further, in one aspect, the composition is lyophilized or otherwise desiccated prior to packaging in the vessel, to be hydrated, e.g., on ice, immediately before use. In another aspect, the composition is frozen, e.g., to from −80° C. to −20° C., prior to packaging in the vessel, to be thawed, e.g., on ice, immediately before use. In a further aspect, the vessel comprises the polymer composition, e.g., in liquid, dried, or frozen form, and a second vessel is provided that comprises the porogen, which is added by an end-user prior to, e.g., immediately prior to, use. In another aspect, the kit comprises a vessel comprising the polymer composition, a second vessel comprising the ECM composition, and a third vessel comprising the porogen, some or all being provided in liquid, dried (e.g., lyophilized or in crystal form), or frozen state. In yet another aspect, the kit comprises a vessel comprising the polymer composition, the ECM composition, and the porogen, provided in liquid, dried (e.g., lyophilized or in crystal form), or frozen state. A vessel is any suitable container, such as without limitation, a vial, a bag, a Mylar package, a tube, a cartridge, etc. In the case of a cartridge, one or more ingredients are stored in one or more compartments of the cartridge. For example, a cartridge may comprise three compartments, one containing the polymer composition, one containing the ECM material, and one containing the porogen. The cartridge may be designed or configured to operate in an automated or manual reconstitution, mixing, and/or delivery device or instrument, such that the instrument, in operation reconstitutes the ingredients, mixes the ingredients, and/or delivers the composition in a manual, partially-automated, or automated manner.

Polymer Composition

The polymer composition is injectable and forms a gel once injected into a patient. The polymer composition may include synthetic polymers, natural polymers, and mixtures or hybrids thereof. In one aspect, the polymer composition is reverse-gelling, and forms a gel at physiological temperature, e.g., 37° C. In another aspect, the polymer composition is an injectable solution and is chemically cross-linked once injected with a suitable crosslinker, or otherwise cross-linked, to form a gel. In another aspect, the polymer composition is shear-thinning, and is either self-healing upon injection, meaning the composition will re-gel (heal) once no shear force is applied, or is chemically-crosslinked or otherwise crosslinked after injection, e.g., with an appropriate crosslinking agent.

In one aspect, the polymer composition can be injected and is cross-linked in vivo, for instance chemically cross-linked with a crosslinker or ionically crosslinked. Polymers that can be cross-linked, or that can be modified and cross-linked include natural polymers (biopolymers), such as polysaccharides, glycosaminoglycans, proteoglycans, and proteins, including, for example and without limitation: alginate (e.g., crosslinked with $Ca^{2+}$ or $Zn^{2+}$ cations), chitosan, hyaluronic acid, collagen, and gellan gum. Non-limiting examples of crosslinking mechanisms include: Michael addition reaction between thiol and vinyl groups, click reaction between bis(yne) molecules and multiarm azides, Schiff base reaction, hydrophobic interactions, ionic interactions, stereocomplex formation, complementary pair formation, and host-guest interactions.

In another aspect, the composition is shear-thinning and optionally self-healing or crosslinkable. Non-limiting examples of suitable shear-thinning polymer compositions, that optionally may be injected with a suitable cross-linker and cross-linked in vivo include: phenylboronic acid and cis-diol modified poly(ethylene glycol); hyaluronic acid encompassed both shear-thinning and self-healing behaviors via guest-host bonding; chitin-poly(lactide-co-glycolide) (PLGA); and Xanthan gum and methylcellulose.

In one aspect, the composition is reverse-gelling. The composition of each component in the polymer composition determines the reverse-gelling capacity, or lower critical solution temperature (LCST), of the composition. At a temperature less than the gelling temperature, the hydrogel flows easily and can be injected into the desired shape. When the temperature is increased above the gelling temperature, e.g., to 37° C., the hydrogel solidifies and retains its shape. Once solidified, the hydrogel is highly flexible and relatively strong at physiological temperature.

The monomer feed ratio and hence the monomer residue composition of any copolymer composition as described herein can be varied so long as the resultant copolymer can be used to manufacture composition as described herein. Variations in the monomer residue composition of copolymer compositions described herein can be readily accomplished and evaluated by one of ordinary skill in the art for usefulness.

Ester, or other labile component, within the copolymer or macromer introduces degradability into the copolymer. Without being bound to this theory, it is understood that for complete removal of the copolymer, the copolymer includes hydrolytically (or otherwise)-cleavable bonds that results in soluble, non-toxic by-products, even above the gelling temperature of the non-degraded copolymer. Once the copolymer is degraded, the gelling temperature of the products is above physiological temperature, which results in dissolution of the degraded hydrogel and clearance of the degraded components. Thus, in one aspect, the copolymer has a gelling temperature (e.g., LCST) below 37° C., in another aspect, between 10° C. and 34° C., and in another aspect, less than 20° C. According to one embodiment, the copolymer has a gelling temperature above 37° C. after its bonds are hydrolyzed or otherwise degraded.

The polymer may comprise a polyester macromer, for example and without limitation, a polyester macromer comprising methacrylate-polylactide residues. In one aspect, the ratio of methacrylate and lactide residues in the polyester macromer is from 1:2 (methacrylate:lactide) to 1:8, in another aspect, from 1:1 to 1:10, such as 1:1, 1:2, 1:3, 1:4, 1:5, 1:6, 1:7, 1:8, 1:9, and 1:10. In another non-limiting example, the polyester macromer comprises hydroxyethyl methacrylate and trimethylene carbonate residues. In aspects, the ratio of hydroxyethyl methacrylate and trimethylene carbonate residues in the polyester macromer ranges from 1:1 to 1:10, 1:2 to 1:5 or any increment within those ranges, including 1:1, 1:2, 1:3, 1:4, 1:4.2, 1:5, 1:6, 1:7, 1:8, 1:9, and 1:10.

In another non-limiting example, the synthetic polymeric component comprises any hydrolytically, chemically, biochemically, and/or proteolytically labile group, non-limiting examples of which include an ester moiety, amide moiety, anhydride moiety, specific peptide sequences, and generic peptide sequences.

A number of biocompatible, biodegradable elastomeric (co)polymers are known and have been established as useful in preparing cell growth matrices. Non-limiting examples of a bioerodible polymer useful in the compositons described herein, include: a polyacrylate or polymethacrylate, a polyacrylamide or polymethacrylamide, a polyester, a polyester-containing copolymer, a polyanhydride, a polyanhydride-containing copolymer, a polyorthoester, and a polyorthoester-containing copolymer. In one aspect, the polyester or polyester-containing copolymer is a poly(lactic-co-glycolic) acid (PLGA) copolymer. In other aspects, the bioerodible polymer is selected from the group consisting of poly(lactic acid) (PLA); poly(trimethylene carbonate) (PTMC); poly(caprolactone) (PCL); poly(glycolic acid) (PGA); poly(glycolide-co-trimethylenecarbonate) (PGTMC); poly(L-lactide-co-glycolide) (PLGA); polyethylene-glycol (PEG-) containing block copolymers; and polyphosphazenes. Additional bioerodible, biocompatible polymers include: a poly(ester urethane) urea (PEUU); poly(ether ester urethane)urea (PEEUU); poly(ester carbonate)urethane urea (PECUU); poly(carbonate)urethane urea (PCUU); a polyurethane; a polyester; a polymer comprising monomers derived from alpha-hydroxy acids such as: polylactide, poly(lactide-co-glycolide), poly(L-lactide-co-caprolactone), polyglycolic acid, poly(dl-lactide-co-glycolide), and/or poly(l-lactide-co-dl-lactide); a polymer comprising monomers derived from esters including polyhydroxybutyrate, polyhydroxyvalerate, polydioxanone, and/or polyglactin; a polymer comprising monomers derived from lactones including polycaprolactone; or a polymer comprising monomers derived from carbonates including polycarbonate, polyglyconate, poly(glycolide-co-trimethylene carbonate), or poly(glycolide-co-trimethylene carbonate-co-dioxanone).

In another aspect (see, e.g., International Patent Application Publication No. WO 2015/160793, which is incorporated herein by reference for its technical disclosure), copolymers comprise, are prepared from, or consist essentially of combinations of three types of subunits/residues: 1) N-alkyl acrylamide in which the alkyl is methyl, ethyl, propyl, isopropyl or cyclopropyl, for example, N-isopropylacrylamide; 2) N-vinylpyrrolidone (VP); and 3) a methacrylate-polylactide (MAPLA) macromer. In non-limiting examples, the MAPLA macromer has a lactide:methacrylate ratio of at least 1:1, or in the range of 2-4:1 (that is, ranging from 2:1 to 4:1). In some embodiments, the feed ratio for NIPAAm:VP:MAPLA is 75-85:5-20:5-10, wherein (NIPAAm+MAPLA):(VP)=85-95:5-15 (inclusive of values between those provided here). In one aspect, the feed ratio of NIPAAm:VP:MAPLA is in the range of 70-90:5-20:5-20. In one example, the feed ratio of VP is 10, such that the feed ratio of NIPAAm:VP:MAPLA is 75-85:10:5-10, for example and without limitation, in one aspect, the feed ratio of NIPAAm:VP:MAPLA is be one of 80:10:10 or 85:10:5. In another embodiment, the feed ratio of VP is 15, such that the feed ratio of NIPAAm:VP:MAPLA is 75-85:15:5-10. In one aspect the feed ratio is 80:15:5. In another aspect, the composition feed ratio is NIPAAm 60%-90%, VP+MAPLA 40%-10%.

The degradation rate is positively correlated to the amount of VP included in the composition, that is, less VP leads to decreased degradation. Degradation of a copolymer hydrogel formed as described herein is typically 200 days and less, depending on VP content. Those of skill will easily be able to fine-tune the VP content to match a preferred degradation rate. As described above, by degradation it is meant that the copolymer (and/or hydrogel formed from said copolymer) is substantially degraded at the indicated time point, with percentage degraded (or percentage remaining) being as described above. In some embodiments, the hydrogel degrades in less than 100 days, less than 90 days, less than 80 days, less than 70 days, less than 60 days, less than 50 days, less than 40 days, less than 30 days, less than 20 days, less than 10 days, or less than 5 days.

According to another aspect, the copolymers comprise, are prepared from, or consist essentially of combinations of four types of subunits/residues: 1) N-alkyl acrylamide in which the alkyl is methyl, ethyl, propyl, isopropyl or cyclopropyl, for example, N-isopropylacrylamide; 2) HEMA; 3) a methacrylate-polylactide (MAPLA) macromer; and 4) a methacrylic acid (MAA). In non-limiting examples, the MAPLA macromer has a lactide:methacrylate ratio of at least 1:1, or in the range of 2-3:1 (that is, ranging from 2:1 to 3:1). In aspects, the feed ratio is 75-85:5-10:3-14.5:0.5-2, wherein (NIPAAm+MAPLA):(HEMA+MAA)=85-95:5-15 (inclusive of values between those provided here). In one example, the feed ratio of HEMA is 10, such that the feed ratio of NIPAAm:HEMA:MAPLA is 75-85:10:5-15, for example and without limitation, in this embodiment, the feed ratio of NIPAAm:HEMA:MAPLA might be one of 84:10:6, 82:10:8 and 80:10:10. In another aspect, the feed ratios of NIPAAm:HEMA:MAPLA:MAA are between 80:5:10:5 and 80:9.5:10:0.5. In another aspect, the feed ratios of NIPAAm:(HEMA+MAPLA+MAA) ranges from (75 to 85):(15 to 25).

The degradation rate of this copolymer is positively correlated to the amount of MAA included in the composition. Degradation of a copolymer hydrogel formed as described herein may be 200 days and less, depending on MAA content. Those of skill will easily be able to fine-tune the MAA content to match a preferred degradation rate. By degradation it is meant that the copolymer (and/or hydrogel formed from said copolymer) is substantially degraded at the indicated time point, for example and without limitation, 80%, 85%, 90%, 95%, 99%, or 99.9% degraded (that is, 20%, 15%, 10%, 5%, 1%, or 0.1% remaining at the indicated time point). In some embodiments, the hydrogel degrades in less than 100 days, less than 90 days, less than 80 days, less than 70 days, less than 60 days, less than 50 days, less than 40 days, less than 30 days, less than 20 days, less than 10 days, or less than 5 days.

According to yet another aspect, copolymers comprise, are prepared from, or consist essentially of four types of subunits/residues: 1) N-alkyl acrylamide in which the alkyl is methyl, ethyl, propyl, isopropyl or cyclopropyl, for example N-isopropylacrylamide; 2) acrylic acid (AAc); 3) a hydroxyethyl methacrylate-poly(trimethylene carbonate) (HEMAPTMC) macromer; and 4) an MAA macromer monomer. In non-limiting examples, the HEMA-poly(trimethylene carbonate) macromer has a TMC:HEMA ratio of at least 1:1, or in the range of 2-3:1 (that is, ranging from 2:1 to 3:1). In other non-limiting examples, the feed ratio of NIPAAm:AAc:HEMAPTMC is 85-87:3-5:10, for example, 86-87:3-4:10.

In other non-limiting aspects, the feed ratio (the molar ratio of monomers in the polymerization reaction used to prepare the copolymer) of NIPAAm:HEMAPTMC is 75-85:2-14.5 (inclusive of values between those provided here), with a feed ratio of MAA being in the range of 0.5-2. In another aspect, the feed ratios of NIPAAm:HEMAPTMC:MAA are between 80:10:5 and 80:10:0.5. In a further aspect, the feed ratio range for NIPAAm:(HEMAPTMC+MAA) is (70-90):(30-10). The degradation rate of the copolymer is directly proportional to the amount of MAA included in the composition. Those of skill will understand that feed ratios of the other constituents of the copolymer may be adjusted to any useful range. Degradation of a copolymer hydrogel formed as described herein may be 200 days and less, depending on MAA content. Those of skill will easily be able to fine-tune the MAA content to match a preferred degradation rate. In some embodiments, the hydrogel degrades in less than 100 days, less than 90 days, less than 80 days, less than 70 days, less than 60 days, less than 50 days, less than 40 days, less than 30 days, less than 20 days, less than 10 days, or less than 5 days.

In addition to characterization by feed ratio, copolymers described herein may be characterized by the ratio of incorporated monomer/macromer residue. For example, and without limitation, copolymers described herein may include NIPAAm:HEMA:MAPLA:MAA, NIPAAm:AAc:HEMAPTMC:MAA, or NIPAAm:VP:MAPLA in ratios similar to those described above regarding feed ratios. Those of ordinary skill in the art will understand that due to polymerization, copolymers may comprise, by molar percentage, as follows:

NIPAAm:HEMA:MAPLA:MAA 71.5-92.5:2.5-16:4.5-11:0.5-2.5, or 72-88:3-15:4.5-11:0.5-2;

NIPAAm:AAc:HEMAPTMC:MAA 71.5-94:2.5-16:4.5-11:0.5-2.5, or 72-88:3-15:4.5-11:0.5-2; and NIPAAm:VP:MAPLA 63-93:4-22:3-22, or 68-92.5:4.5-21:3-21.

In one aspect, the incorporated molar ratio of monomer and macromer residues for NIPAAm:VP:MAPLA is 85-88:6-12:2-7. Those of skill will understand that final incorporated amounts of residues may vary from the feed ratio that is utilized by up to 10%, inclusive of values within that range, for example, 3%

According to another aspect, the copolymer comprises N-isopropylacrylamide (NIPAAm) residues, hydroxyethyl methacrylate (HEMA) residues and methacrylate-polylactide (MAPLA) macromer residues. Alternately, the copolymer comprises N-isopropylacrylamide residues, acrylic acid (AAc) residues, and hydroxyethyl methacrylate-poly(trimethylene carbonate) (HEMAPTMC) macromer residues.

Although the size of the copolymers can vary, in one example, the copolymer has an Mn of between 20 kD and 35 kD. In another example, the copolymer has a polydispersity index (PDI, Mw/Mn) of between 1 and 2 (see, e.g., U.S. Pat. Nos. 8,673,295, and 9,408,855, which are incorporated herein by reference for their technical disclosure).

In each copolymer, the ratio of the constituents of the macromer may be varied. For example and without limitation, the polyester macromer is a poly(trimethylene carbonate (TMC)-containing macromer), consisting essentially of or consisting of hydroxyethyl methacrylate residues and varying numbers of trimethylene carbonate units/residues. In another embodiment, the polyester macromer is a methacrylate-polylactide macromer comprising methacrylate residues and varying numbers of lactide residues. See, also, U.S. Pat. No. 8,889,791 and United States Patent Application Publication No. 2017/0028101.

For the polymer compositions useful in the present invention, each monomer or macromer contributes to the desired physical properties of the hydrogel to enable an injectable material for injection into empty cavities for wounds or tissue repair. An optional amine-reactive component may be included in the copolymer. The amine-reactive group can be a succinimide group, an oxysuccinimide group or an isocyanate group, such as is produced by incorporation of N-hydroxysuccinimide methacrylate (MANHS) or N-acryloxy succinimide (NAS) monomers into the copolymer. The amine-reactive groups bind to amine-containing compounds including biomolecules such as collagen and/or other bioactive or biocompatible materials or factors.

In aspects, diamines and diols are useful building blocks for preparing the (co)polymer compositions described herein. Diamines as described above have the structure $H_2N-R-NH_2$ where "R" is an aliphatic or aromatic hydrocarbon or a hydrocarbon comprising aromatic and aliphatic regions. The hydrocarbon may be linear or branched. Examples of useful diamines are putrescine (R=butylene) and cadaverine (R=pentylene). Useful diols include polycaprolactone (e.g., Mw 1000-5000), multi-block copolymers, such as polycaprolactone-PEG copolymers, including polycaprolactone-b-polyethylene glycol-b-polycaprolactone triblock copolymers of varying sizes. Other building blocks for useful diols include, without limitation glycolides (e.g., polyglycolic acid (PGA)), lactides, dioxanones, and trimethylene carbonates. Diisocyanates have the general structure OCN—R—NCO, where "R" is an aliphatic or aromatic hydrocarbon or a hydrocarbon comprising aromatic and aliphatic regions. The hydrocarbon may be linear or branched.

In a one aspect, the polymer composition comprises a biodegradable poly(ester urethane) urea (PEUU), poly(ether ester urethane)urea (PEEUU), poly(ester carbonate)urethane urea (PECUU), or poly(carbonate)urethane urea (PCUU). In some examples, the composition comprises poly(ester-urethane)urea (PEUU). PEUU can be synthesized using putrescine as a chain extender and a two-step solvent synthesis method. For example, a poly(ester urethane) urea elastomer (PEUU) may be made from polycaprolactonediol (MW 2,000) and 1,4-diisocyanatobutane, with a diamine, such as putrescine as the chain extender. A suitable PEUU polymer may be made by a two-step polymerization process whereby polycaprolactone diol (Mw 2,000), 1,4-diisocyanatobutane, and putrescine are combined in a 1:2:1 molar ratio though virually any molar feed ratio may suffice so long as the molar ratio of each monomer component is >0. In one aspect, the molar feed ratio of polycaprolactone diol plus putrescine is equal to that of diisocyanatobutane. A poly (ether ester urethane) urea elastomer (PEEUU) may be made by reacting polycaprolactone-b-polyethylene glycol-b-polycaprolactone triblock copolymers with 1,4-diisocyanatobutane and putrescine. In one aspect, PEEUU is obtained by a two-step reaction using a 2:1:1 reactant stoichiometry of 1,4-diisocyanatobutane:tri block copolymer: putrescine.

In another aspects, the composition comprises a poly (ester carbonate urethane)urea (PECUU) or a poly(carbonate)urethane urea (PCUU) material. PECUU and PCUU are described, for example, in Hong et al. (Tailoring the degradation kinetics of poly(ester carbonate urethane)urea thermoplastic elastomers for tissue engineering scaffolds Biomaterials, doi:10.1016/j.biomaterials.2010.02.005). PECUU is synthesized, for example, using a blended soft segment of polycaprolactone (PCL) and poly(1,6-hexamethylene carbonate) (PHC) and a hard segment of 1,4-diisocyanatobutane (BDI) with chain extension by putrescine. Different molar ratios of PCL and PHC can be used to achieve different physical characteristics. Putrescine is used as a chain extender by a two-step solvent synthesis method. In one example, the (PCL+PHC):BDI:putrescine molar ratio is defined as 1:2:1.

ECM Material

An "ECM material," is a decellularized and/or devitalized material comprising or that is prepared from an extracellular matrix-containing tissue, and does not solely consist of a single, isolated and purified ECM component, such as a purified collagen preparation, as are commercially available. Any type of tissue-derived material can be used to produce the ECM materials in the methods, compositions and devices as described herein (see generally, U.S. Pat. Nos. 4,902,508; 4,956,178; 5,281,422; 5,352,463; 5,372,821; 5,554,389; 5,573,784; 5,645,860; 5,711,969; 5,753,267; 5,762,966; 5,866,414; 6,099,567; 6,485,723; 6,576,265; 6,579,538; 6,696,270; 6,783,776; 6,793,939; 6,849,273; 6,852,339; 6,861,074; 6,887,495; 6,890,562; 6,890,563; 6,890,564; and 6,893,666). The ECM material may be protease-, or otherwise-solubilized ECM material, such as ECM material that is acid-protease solubilized in acidic conditions—producing a reverse-gelling composition. In certain aspects, the ECM material is isolated from a vertebrate animal, for example and without limitation, from a mammal, including, but not limited to, human, monkey, pig, cow and sheep. The ECM material can be prepared from any organ or tissue, including, without limitation, urinary bladder, intestine, liver, esophagus, blood vessel, liver, nerve or brain, or dermis.

In various aspects, ECM material is decellularized, sterilized and/or dried by any useful method. ECM-derived material can then be used in any form in the methods and compositions described herein. In certain aspects, in the context of depositing the ECM material to prepare the composition described herein, the ECM material is either finely comminuted, e.g., into micro-scale-sized (from 1-999 microns) or nano-scale-sized (from 1-999 nanometers) particles, or is solubilized, for example, in the form of solution, a pre-gel or gel, as described below.

The ECM material can be sterilized by any of a number of methods without loss of its ability to induce endogenous tissue growth. For example, the material can be sterilized by propylene oxide or ethylene oxide treatment, gamma irradiation treatment (0.05 to 4 mRad), gas plasma sterilization, peracetic acid sterilization, or electron beam treatment. Traditionally, ECM material is disinfected by immersion in 0.1% (v/v) peracetic acid (σ), 4% (v/v) ethanol, and 96% (v/v) sterile water for 2 h. The ECM material is then washed twice for 15 min with PBS (pH=7.4) and twice for 15 min with deionized water. International Patent Application Publication No. WO 2015/143310, incorporated herein by reference, describes further methods for sterilization of ECM materials.

Commercially-available ECM preparations can also be used in various aspects of the methods, devices and compositions described herein. In one aspect, the ECM is derived from small intestinal submucosa or SIS. Commercially available preparations include, but are not limited to, Surgisis™, Surgisis-ES™, Stratasis™, and Stratasis-ES™ (Cook Urological Inc.; Indianapolis, Ind.) and GraftPatch™ (Organogenesis Inc.; Canton Mass.). In another embodiment, the ECM is derived from dermis. Commercially available preparations include, but are not limited to Pelvicol™ (crosslinked porcine dermal collagen, sold as Permacol™ in Europe; Bard Medical Division, Covington, Ga.), Repliform™ (Microvasive; Boston, Mass.) and Alloderm™ (LifeCell; Branchburg, N.J.). In another embodiment, the ECM is derived from urinary bladder. Commercially available preparations include, but are not limited to UBM (Acell Corporation; Jessup, Md.).

The composition described herein comprises, in one aspect an extracellular matrix-derived gel (see, e.g., U.S. Pat. Nos. 8,361,503, and 8,691,276). In its broadest sense, ECM-derived scaffold materials are comminuted and solubilized to form a hydrogel. The solubilized hydrogel may or may not be dialyzed at any stage prior to solubilization, and in one aspect is not dialyzed prior to or after solubilization. Solubilization may be achieved by digestion with a suitable acid protease, such as chymotrypsin, pepsin, papain or elastase, under acidic conditions, such as between pH 1-4, or pH 1.5-2.5, e.g. pH 2.0, or in 0.01N HCl. In examples, the method for making such a gel comprises: (i) comminuting devitalized and/or decellularized tissue, (ii) solubilizing non-dialyzed or non-cross-linked devitalized and/or decellularized tissue by digestion with an acid protease in an acidic solution to produce a digest solution, (iii) raising the pH of the digest solution to a pH between 7.2 and 7.8 to produce a neutralized digest solution, and (iv) gelling the solution at a temperature greater than the gelation temperature (e.g., LCST) of the neutralized digest solution, typically greater than 25° C. or room temperature, thereby producing an ECM gel. In the context of the present invention, the neutralized digest solution (pre-gel, that is optionally lyophilized) is mixed with the reverse-gelling polymer, and the porogen prior to implantation (e.g., injection) into a patient.

In one aspect of the solubilization of devitalized and/or decellularized tissue, the devitalized and/or decellularized tissue is solubilized with an acid protease. The acid protease may be, without limitation, pepsin. The material typically is solubilized at an acid pH suitable or optimal for the protease, such as greater than about pH 2, or between pH 1 and 4, or pH 1.5-2.5, for example, in a 0.01N HCl solution. The material typically is solubilized for 12-48 hours, depending upon the tissue type (e.g., see examples below), with mixing (stirring, agitation, admixing, blending, rotating, tilting, etc.) often on ice, at 4° C. or at room temperature (e.g., 20° C. to 23° C.). Once the material is solubilized, the pH is raised to between 7.2 and 7.8, and according to one embodiment, to pH 7.4. Bases, such as bases containing hydroxyl ions, including NaOH, can be used to raise the pH of the solution. Likewise buffers, such as an isotonic buffer, including, without limitation, Phosphate Buffered Saline (PBS), can be used to bring the solution to a target pH, or to aid in maintaining the pH and ionic strength of the gel to target levels, such as physiological pH and ionic conditions. The neutralized digest solution can be gelled at temperatures approaching 37° C., typically at any temperature over 25° C., though gelation proceeds much more rapidly at temperatures over 30° C., and as the temperature approaches physiological temperature. The method, according to one aspect, does not include a dialysis step prior to gelation, yielding a more-complete ECM-like matrix that typically gels at 37° C. more slowly than comparable collagen or dialyzed ECM preparations.

Porogen

A porogen is a particle that can be mixed into the composition described herein, and which dissolves over time, leaving pores in the solidified matrix. In aspects, useful porogens for the compositions described herein dissolve within 48 hours, or within 24 hours of gelation of the composition, and do not substantially dissolve in the time period they are mixed within the polymer/ECM material mixture prior to injection and gelation. For in vivo use, the porogen is biocompatible, in that it is acceptably safe for administration to a patient in the compositions described herein. Sugar particles, and salt particles can be used as porogens so long as they do not dissolve too rapidly or cause untoward effects, such as electrolyte imbalances or undesirable pH fluctuations, in the patient when administered in the compositions described herein. PVA and PEG particles may be used as porogens, but should be selected for molecular weights that dissolve appropriately—that is they do not substantially dissolve prior to gelation of the composition in situ, and within 48 or 24 hours, and preferably within 24 hours of administration of the composition to a patient. The rapid dissolution of the porogen particles is desirable to accommodate early-arriving cells, such as macrophage and neutrophils, and initiating appropriate response and infiltration. Other biocompatible (e.g., pharmaceutically-acceptable) particles, e.g., oligomeric or polymeric particles, nanoparticles, etc., can be used so long as they substantially remain as particles until the composition gels, and dissolve, erode, etc. within an appropriate time frame, e.g., less than 24 hours once the composition gels. In one aspect, the porogen is a mannitol particle. Mannitol was chosen in the example below for its solubility characteristics: being less soluble at low temperature and more soluble at body temperature, and having limited solubility so that the porogen particles substantially remain as solids until the reverse-gelling composition forms a gel after implantation. Porogen particles can be any size effective to produce pores of an adequate size to infiltrate the matrix in vivo once the porogen dissolves. As an example, particle/pore size of between 30 µm and 300 µm (micrometers, microns) is expected to be effective. The amount of porogen used should be such that a sufficient number of pores are made, and not so much as to affect the integrity of the gel matrix.

Therapeutic Agents

In certain aspects, the composition described herein comprises one or more therapeutic agents. For example, at least one therapeutic agent is added to the composition described herein before it is implanted in the patient or otherwise administered to the patient. Generally, the therapeutic agents include any substance that can be coated on, embedded into, absorbed into, adsorbed to, or otherwise attached to or incorporated onto or into the composition described herein or incorporated into a drug product that would provide a therapeutic benefit to a patient. Non-limiting examples of such therapeutic agents include: growth factors, chemoattractants, cytokines, antimicrobial agents, emollients, retinoids, and topical steroids. Each therapeutic agent may be used alone or in combination with other therapeutic agents. For example and without limitation, a composition comprising neurotrophic agents or cells that express neurotrophic agents may be applied to a wound that is near a critical region of the central nervous system, such as the spine.

Active agents that may be incorporated into the compositions described herein include, without limitation, anti-inflammatories, such as, without limitation, nitro-fatty acids NSAIDs (non-steroidal anti-inflammatory drugs) such as salicylic acid, indomethacin, sodium indomethacin trihydrate, salicylamide, naproxen, colchicine, fenoprofen, sulindac, diflunisal, diclofenac, indoprofen sodium salicylamide, antiinflammatory cytokines, and antiinflammatory proteins or steroidal anti-inflammatory agents); antibiotics; anticlotting factors such as heparin, Pebac, enoxaprin, aspirin, hirudin, plavix, bivalirudin, prasugrel, idraparinux, warfarin, coumadin, clopidogrel, PPACK, GGACK, tissue plasminogen activator, urokinase, and streptokinase; growth factors. Other active agents include, without limitation: (1) immunosuppressants; glucocorticoids such as hydrocortisone, betamethisone, dexamethasone, flumethasone, isoflupredone, methylprednisolone, prednisone, prednisolone, and triamcinolone acetonide; (2) antibodies; (3) drugs acting on immunophilins, such as cyclosporine, zotarolimus, everolimus, tacrolimus and sirolimus (rapamycin), interferons, TNF binding proteins; (4) taxanes, such as paclitaxel and docetaxel; statins, such as atorvastatin, lovastatin, simvastatin, pravastatin, fluvastatin and rosuvastatin; (5) nitric oxide donors or precursors, such as, without limitation, Angeli's Salt, L-Arginine, Free Base, Diethylamine NONOate, Diethylamine NONOate/AM, Glyco-SNAP-1, Glyco-SNAP-2, S-Nitroso-N-acetylpenicillamine, S-Nitrosoglutathione, NOC-5, NOC-7, NOC-9, NOC-12, NOC-18, NOR-1, NOR-3, SIN-1, Hydrochloride, Sodium Nitroprusside, Dihydrate, Spermine NONOate, Streptozotocin; and (6) antibiotics, such as, without limitation: acyclovir, afloxacin, ampicillin, amphotericin B, atovaquone, azithromycin, ciprofloxacin, clarithromycin, clindamycin, clofazimine, dapsone, diclazaril, doxycycline, erythromycin, ethambutol, fluconazole, fluoroquinolones, foscarnet, ganciclovir, gentamicin, iatroconazole, isoniazid, ketoconazole, levofloxacin, lincomycin, miconazole, neomycin, norfloxacin, ofloxacin, paromomycin, penicillin, pentamidine, polymixin B, pyrazinamide, pyrimethamine, rifabutin, rifampin, sparfloxacin, streptomycin, sulfadiazine, tetracycline, tobramycin, trifluorouridine, trimethoprim sulfate, Zn-pyrithione, ciprofloxacin, norfloxacin, afloxacin, levofloxacin, gentamicin, tobramycin, neomycin, erythromycin, trimethoprim sulfate, polymixin B and silver salts such as chloride, bromide, iodide and periodate.

Any useful cytokine or chemoattractant can be mixed into, mixed with, or otherwise combined with any composition as described herein. For example and without limitation, useful components include growth factors, interferons, interleukins, chemokines, monokines, hormones, and angiogenic factors. In certain non-limiting aspects, the therapeutic agent is a growth factor, such as a neurotrophic or angiogenic factor, which optionally may be prepared using recombinant techniques. Non-limiting examples of growth factors include basic fibroblast growth factor (bFGF), acidic fibroblast growth factor (aFGF), vascular endothelial growth factor (VEGF), hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF), corticotrophin releasing factor (CRF), transforming growth factors α and β (TGF-α and TGF-β), interleukin-8 (IL-8), granulocyte-macrophage colony stimulating factor (GM-CSF), interleukins, and interferons. Commercial preparations of various growth factors, including neurotrophic and angiogenic factors, are available from R & D Systems, Minneapolis, Minn.; Biovision, Inc, Mountain View, Calif.; ProSpec-Tany TechnoGene Ltd., Rehovot, Israel; and Cell Sciences®, Canton, Mass.

In certain aspects, cells are added to the material. Non-limiting examples of useful cells include: stem cells, progenitor cells and differentiated cells; recombinant cells; muscle cells and precursors thereof; nerve cells and precursors thereof; mesenchymal progenitor or stem cells; bone cells or precursors thereof, such as osteoprogenitor cells.

Any useful cytokine, chemoattractant, drug or cells can be mixed into, mixed with, co-applied or otherwise combined with any material as described herein. For example and without limitation, useful components include growth factors, interferons, interleukins, chemokines, monokines, hormones, angiogenic factors, drugs and antibiotics. Cells can be mixed into the material or can be included on or within a sheet, tube or other device, such as a biological scaffold, combined with the decellularized colonic extracellular matrix material. In either case, when the substrate is seeded with cells, the cells can be grown and/or adapted to the niche created by incubation in a suitable medium in a bioreactor or incubator for a suitable time period to optimally/favorably prepare the composition for implantation in a patient. The substrate can be seeded with cells to facilitate in-growth, differentiation and/or adaptation of the cells. For example and without limitation, the cells can be autologous or allogeneic with respect to the patient to receive the composition/device comprising the gel. The cells can be stem cells or other progenitor cells, or differentiated cells. In one example, a layer of dermis obtained from the patient is seeded on a mold, for use in repairing damaged skin and/or underlying tissue. In another aspect, the composition according to any aspect described herein is cell-free, that is, it does not contain living cells, but after implantation, native cells migrate into the matrix that is formed in situ from the patient.

In another aspect, antioxidants are added to the polymeric composition, such as organic or inorganic antioxidants. In one aspect, the antioxidant is a nanoparticle incorporated by any means into the polymer composition, such as, for example, a cerium nanoparticle. As an example, cerium nanoparticles are included in the injected composition.

Pharmaceutically acceptable salts or prodrugs of any active agent (e.g., therapeutic agent or drug), bound to or otherwise combined with, or incorporated into the composition according to any aspect herein, may be employed. Pharmaceutically acceptable salts are, because their solubility in water is greater than that of the initial or basic compounds, particularly suitable for medical applications. These salts have a pharmaceutically acceptable anion or cation. Suitable pharmaceutically acceptable acid addition salts of the compounds of the invention include, without limitation, salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts include without limitation, ammonium salts, alkali metal salts (such as sodium and potassium salts), alkaline earth metal salts (such as magnesium and calcium salts), and salts of trometamol (2-amino-2-hydroxymethyl-1,3-propanediol), diethanolamine, lysine or ethylenediamine. Pharmaceutically acceptable salts may be prepared from parent compounds by any useful method, as are well known in the chemistry and pharmaceutical arts.

In some examples, the polymer composition further comprises, for example and without limitation, a biomacromolecular component derived from ECM. In one example, the polymer composition comprises the biomacromolecule collagen so that collagenase, which is present in situ, can degrade the collagen. As an example, the polymer composition may comprise one or both of a collagen and an elastin. Collagen is a common ECM component, and typically is degraded in vivo at a rate faster than many synthetic bioerodable polymers. Therefore, manipulation of collagen content in the polymer composition may be used as a method of modifying bioerosion rates in vivo. Collagen may be present in the polymer composition in any useful range, including, without limitation, from about 2% wt. to about 95% wt., preferably in a range of from about 25% wt. to about 75% wt., inclusive of all ranges and points therebetween, including from about 40% wt. to about 75% wt., including about 75% wt. and about 42.3% wt. Elastin may be incorporated into the polymer composition in order to provide increased elasticity. Elastin may be present in the polymer composition in any useful range, including without limitation, from about 2% wt. to about 50% wt., inclusive of all ranges and points therebetween, including from about 40% wt. and about 42.3% wt., inclusive of all integers and all points therebetween and equivalents thereof. In one non-limiting example, collagen and elastin are present in approximately equal amounts in the polymer composition. In another embodiment, the sum of the collagen and elastin content in the polymer composition is in any useful range, including, without limitation, from about 2% wt. to about 95% wt., and preferably in the range of from about 25% wt. to about 75% wt., inclusive of all ranges and points therebetween, including from about 40% wt. to about 75% wt., including about 75% wt. and about 42.3% wt.

In preparation of the composition, and delivery of the composition, the ingredients may be in any useful form to prevent hydrolysis of the polymer, and dissolution of the porogen, at least those ingredients are, in aspects stored and distributed in a dried, lyophilized, or glassified state. As such, the ingredients used to prepare the composition need to be reconstituted and, where necessary, mixed. In one aspect, the compositions are stored in a lyophilized and/or dried state in a single vessel or medical syringe, and are reconstituted and mixed immediately prior to use with, for example and without limitation, water, saline (e.g., normal saline, e.g., 0.9% w/v NaCl in water), or phosphate-buffered saline (PBS). Where ingredients used to prepare the composition are stored in separate vessels or compartments within a cartridge. As above, the cartridge may be designed or configured to operate in an automated or manual reconstitution, mixing, and/or delivery device or instrument, such that the instrument, in operation reconstitutes the ingredients, mixes the ingredients, and/or delivers the composition in a manual, partially-automated, or automated manner. Various commercial devices are available to reconstitute, mix, and/or deliver the composition and its ingredients, including: Mix2Vial® Reconstitution System and Needle-Free Transfer Device (West Pharmaceutical Services, Inc., Exton, Pa.); SmartMix™ Pre-filled Reconstitution System (Yukon Medical, Research Triangle Park, N.C.); and Reconstitution Filling Systems (Enable Injections, Cincinnati, Ohio), and one of ordinary skill may adapt common medical syringes, syringe pumps, and mixers to accomplish the reconstitution, mixing, and/or delivery the composition.

In a further aspect, a kit is provided comprising a template and/or a sheet of a porous deposited biodegradable, elastomeric polymer or ECM derived material described herein in a container, which may be the packaging, or which may be contained within packaging. The container is suitable for storage and transfer of the contents of the kit in commercial distribution routes of the kit.

Example

In this example, the polymer may be synthesized by addition polymerization. Compared to its natural product counterparts, its composition is well-defined and tunable. Specifically, its mechanical properties can be tuned to achieve relatively high stiffness suitable for maintaining tissue shape. The polymer itself and its degradation product are both biocompatible. The porous structure is incorporated into the hydrogel filler. This allows cell infiltration and tissue integration before degradation and adsorption of the polymer component. Injecting particles that dissolve in situ at the site of injection, such as salt or sugar particles (e.g., mannitol) as porogens is a new method to generate porous structure in injectable hydrogels in situ. Mannitol is a useful porogen because it is widely used in clinical applications and bears no toxicity. The bioactive ECM component has been shown to promote cell migration, mediate inflammation, modulate macrophage polarization, and improve wound healing. The compositions an methods described herein combine the bioactivity of ECM and the mechanical effect of thermally-responsive polymer.

Materials & Methods

All chemicals were purchased from Sigma-Aldrich unless otherwise stated. N-isopropylacrylamide (NIPAAm) was purified by recrystallization from hexane and vacuum-dried. 2-Hydroxyethyl methacrylate (HEMA) was purified by vacuum distillation. Vinylpyrrolidone (VP), lactide, benzoyl peroxide (BPO), sodium methoxide ($NaOCH_3$), methacryloyl chloride, methacrylic acid (MAA) and other solvents were used as received. D-mannitol particles were sieved to obtain the portion between 170 and 230 meshes.

Synthesis of methacrylate polylactide (MAPLA): $NaOCH_3$/methanol was added to a lactide/dichloromethane solution to synthesize polylactide (HO-PLA-$OCH_3$) through ring-opening polymerization. MAPLA was synthesized by dropping methacryloyl chloride into an HO-PLA-$OCH_3$/ dichloromethane solution containing triethylamine. Dichloromethane was removed by rotary evaporation, and the product was purified by flash chromatography to obtain MAPLA with yields of ~60%.

Synthesis of poly(NIPAAm-co-VP-co-MAPLA) (VP10): Poly(NIPAAm-co-VP-co-MAPLA) copolymers were synthesized from NIPAAm, VP and MAPLA by free radical polymerization. The feed ratios of NIPAAm, VP and MAPLA were 80/10/10, and the corresponding product polymers were denoted VP10. Monomers (0.066 mol) were dissolved in 180 mL of 1,4-dioxane containing 0.23 g BPO. The polymerization was carried out at 70° C. for 24 h under an argon atmosphere. The copolymer was precipitated in hexane and further purified by precipitation from THF into diethyl ether and vacuum-dried, with yields of ~80%.

Preparation of urinary bladder matrix (UBM) digest: Fresh porcine bladders were obtained and excess connective tissue and residual urine were removed. The tunica serosa, tunica muscularis externa, the tunica submucosa, and the tunica muscularis mucosa were then mechanically removed. The luminal surface was rinsed with 1.0 N saline solution to dissociate urothelial cells of the tunica. The resulting material was composed of the basement membrane of the urothelial cells plus the subadjacent lamina propria, or UBM. UBM sheets were then placed in a 0.1% (v/v) peracetic acid solution, 4% (v/v) ethanol, and 95.9% (v/v) sterile water for 2 h. To remove peracetic acid, UBM was washed twice for 15 min with PBS followed by two 15 min washes with sterile water. UBM sheets were then lyophilized and the lyophilized UBM was powdered using a Wiley mill and filtered through a 60 mesh screen. The powdered material was solubilized at a concentration of 10 mg/mL in 0.1 mg/mL pepsin in 0.01 N HCl at a constant stir rate of 48 h. The UBM digest solution was then frozen until use in further experiments. The digest was neutralized to a pH of 7.4 using NaOH and diluted in phosphate buffered saline (PBS) to the desired concentration.

Hydrogel preparation: Nonporous hydrogel (NP) was prepared by dissolving VP10 in PBS (10 wt %). Nonporous hydrogel with the UBM digest component (NPE, with "E" denoting the extracellular matrix components from UBM digest) was obtained by mixing 20 wt % VP10 in PBS and 10 mg/mL UBM digest (1:1 v/v). Porous hydrogel without the UBM digest component (PM) was prepared by adding 30 wt % mannitol particles to the NP formula and mixing with a syringe. Pores were formed after PM gelation at 37° C. and dissolution of the mannitol particles. Similarly, porous hydrogel with the UBM digest component (PME) was prepared by adding 30 wt % mannitol particles to the NPE formula and mixing with a syringe.

Characterization: Mannitol release from the PM and PME hydrogels were characterized by quantifying the dissolved mannitol in the supernatant of the hydrogel/PBS system. PM or PME hydrogel (0.5 mL) was injected into 10 mL 37° C. PBS in 30 s after mixing the hydrogels with mannitol. Supernatants were collected at different time intervals and replaced with fresh 37° C. PBS. The mannitol in the supernatants was quantified with a mannitol assay (Sigma-Aldrich, USA) and the cumulative release was calculated accordingly.

Subsequent to 24 h gelation in 37° C. PBS, NP, PM and PME hydrogels were frozen in liquid nitrogen, cut to expose the interior and lyophilized. The processed samples were observed by scanning electron microscopy (SEM). The pore sizes of the processed PM and PME hydrogel sections were measured with ImageJ on the micrographs.

To measure the mechanical properties of the hydrogels, samples from the NP, PM and PME groups were incubated in a 37° C. water bath for 24 h to reach a stable water content, obtaining hydrogel discs. An ElectroForce 3200 Series II (Bose, Minn., US) equipped with a 10 N load cell was utilized to record the compression-force curve immediately after the samples were taken out of the water bath. The compression modulus was calculated from these data for each group.

Hydrogel degradation was quantified by mass loss measurements. Hydrogels with known initial dry masses (~40 mg) were immersed in 4 mL of PBS containing 50 U/mL type I collagenase at 37° C. (Since collagen is one of the major structure proteins in UBM products, in the in vitro degradation test collagenase was added to mimic the in vivo enzymatic degradation mechanism for UBM). At predefined time points over a 4 week period, the hydrogels (n=3 each) were lyophilized and the relative mass loss was recorded.

Cell migration study: Bone marrow-derived macrophages were harvested from 2 month old C57/BL6 mice as previously described using methodology approved by the Institutional Animal Care and Use Committee of the University of Pittsburgh. Briefly, femur and tibiae were harvested and separated from muscle and connective tissue. Bones were cut at either end to expose the bone marrow. Sterile syringe and needles were used to flush out bone marrow using macrophage differentiation media (DMEM/10% FBS/10% L-929 Supernatant/1% PenStrep/2% NEAA/1% HEPES/0.2% β-2 mercaptoethanol). Bone marrow lysate was reconstituted in media and filtered through a sterile cell filter. Cells were plated in 6-well plates and cultured for 7 d in media to differentiate them into macrophages.

NP, PM and PME hydrogels (0.5 mL) were immersed in 10 mL DMEM for 24 h without DMEM replacement. The effect of the released products from NP, PM and PME hydrogels on macrophage migration was evaluated with a CytoSelect cell migration assay (Cell Biolabs, USA) according to the manufacturer's instruction. The releasate (500 μL) was added to the lower well of the migration plate. 150,000 macrophages were added to the inside of each insert (n=4 each group). DMEM only was used as control.

Rat hind limb hydrogel injection studies: Adult female Lewis rats weighing 160-210 g were utilized in a protocol that was approved by the University of Pittsburgh's Institutional Animal Care and Use Committee. Anesthesia was induced with 3.0% isoflurane inhalation with 100% oxygen followed by 1.5-2% isoflurane with 100% oxygen during the procedure. Dermatotomy was performed to expose the inner thigh muscles on both legs. Single injections of 200-250 uL of hydrogel were made approximately 3 mm deep in the muscle bed. For each hydrogel, 18 injections in 18 legs were made. For acute studies, the inner thigh muscles from 2 legs each of NP, PM and PME group were excised 3 min after injection. The muscles were incised to expose the hydrogel injection site, and images were taken with a Dino-Lite (AM4113T-GFBW, AnMo Electronics, New Taipei City, Taiwan) under brightfield mode. For longer term studies, after 3 and 21 d, 4 rats from each group at each time point were sacrificed and the inner thigh muscles encompassing the hydrogel injection site were excised, and the tissue was fixed in 10% formaldehyde for 3 d before embedding. Trichrome and immunohistochemical staining with monoclonal antibodies against CD68 (1:200, Abcam, USA), CD86 (1:150, Abcam, USA) and CD206 (1:200, Santa Cruz, USA) were performed. CD68 was co-stained with CD86 and CD206 separately. A red secondary antibody was used for CD68, green secondary antibodies were used for CD86 and CD206. Nuclei were stained with 40',6-diamidino-2-phenylindole (DAPI; 1:10000, Sigma). Microscopic images were taken by fluorescence microscopy.

Cell densities around and in the hydrogel injection sites for each group at day 3 and day 21 were analyzed from the microscopic images using ImageJ. M1 macrophages were identified by CellProfiler as $CD68^+/CD86^+/DAPI$ cells. M2 macrophages were identified by CellProfiler as $CD68^+/CD206^+/DAPI$ cells.

Rabbit adipose tissue defect repair: Female New Zealand rabbits (5 months old, 3.5 kg) were utilized. Anesthesia was induced with ketamine/xylazine and maintained with inhalant isoflurane via nose cone. Dermatotomy was performed to expose the inner thigh adipose tissues on both legs. For the sham group, the wound in the skin was closed 5 min after dermatotomy. For the PBS, fat transplantation and PME gel groups, a 1×1 cm defect was created by removing a section of the fat pad in the center of the adipose tissues. The defect site was marked for identification purposes during explantation with non-absorbable sutures in the corners. For the fat transplantation group, adipose tissue removed from the other leg of the same animal was placed in the defect and sutured to surrounding fat tissue followed by wound closure. For the PBS group, 1 mL PBS was injected into the defect after closing the skin wound. Similarly, 1 mL PME hydrogel was injected into the defect after closing the skin wound for the PME Gel group. Experiments were designed so that different treatments were made in the same rabbit.

At 2 and 8 weeks after surgery, the surgical sites were examined by palpation by the same clinician to compare the stiffness of the underlying tissue with the healthy control group. The perceived tissue stiffness was scored on a 1 to 5 scale with 1 being the most soft and 5 being the most stiff. The rabbits were then sacrificed, and the inner thigh adipose tissue encompassing the defects was excised. The tissue was fixed in 10% formaldehyde for 3 d before embedding. Trichrome staining and Oil Red staining were performed on paraffin sections and frozen sections, respectively. Adipocyte size and density of crown-like structures were analyzed by ImageJ. Isolectin/BIOPSY/DAPI staining was performed on the frozen sections.

Statistical analyses: For paired comparisons, a t-test was employed. Where three or more groups were being compared, one-way ANOVA was employed with Tukey's test applied for specific comparisons. Results are presented as the mean with standard deviation. Kruskal-Wallis and Mann-Whitney test (non-parametric) were used to evaluate the differences among scored tissue stiffness. Statistical significance was defined as p<0.05.

Results

Porous hydrogel formation: Sieved mannitol particles have an initial size of 68.0 µm. After mixing with the VP10 hydrogel solution for 10 min, the particle size did not decrease significantly. In addition, there was no size difference between particles mixed with or without UBM digest in the hydrogel. After injecting the hydrogel/mannitol mixtures into 37° C. PBS, the mixtures instantly solidified, and mannitol was rapidly dissolved and released from the hydrogel mass. After 24 h, 80% of the mannitol was released from the hydrogel of PM group, whereas 100% of the mannitol was released from the hydrogel of PME group.

Figure 1:
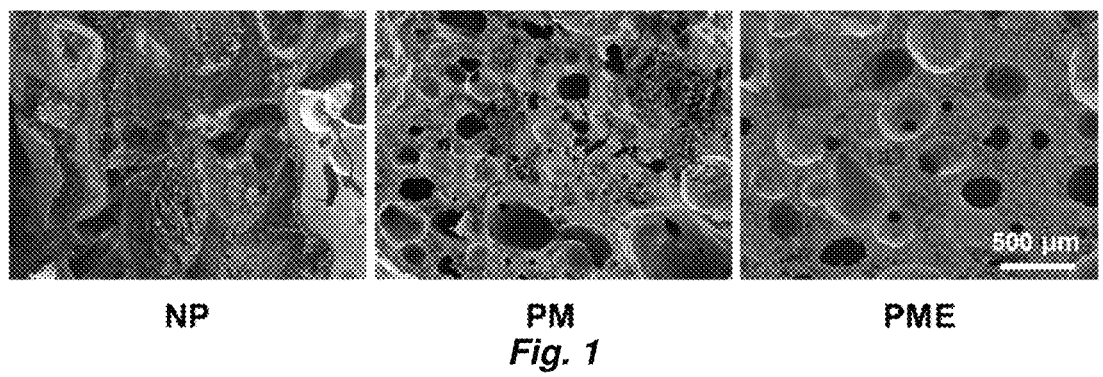
FIG. 1 shows hydrogel cross-sections. NP: nonporous hydrogel, PM: nonporous hydrogel without the UBM digest component, PME: porous hydrogel with the UBM digest component.

Densely packed pores can be observed in the hydrogels of PM and PME groups after 24 h of gelation, as opposed to the nonporous hydrogel mass of the NP group (FIG. 1). The majority of the pores found in PM and PME groups were elliptical. The pore size of PM group was 237±80 µm, significantly smaller than the pore size of PME group, which was 295±87 µm. In addition, channels wider than 50 µm could be observed on the walls of the pores, creating interconnected pores (FIG. 1).

Release of UBM component: Matrix-bound vesicles (MBVs) were found by Transmission electron microscope (TEM) in the supernatant 2 min after hydrogel immersion in 37° C. PBS. The MBVs showed a typical size as previously reported and remained intact (L. Huleihel, et al., Matrix-bound nanovesicles within ECM bioscaffolds, *Science Advances*. (2016) 10;2(6):e1600502. doi: 10.1126/sciadv.1600502). The protein content of UBM mixed in the hydrogel was rapidly released. 48% of the total protein was released within 30 min of gelation, 70% was released after 24 h gelation.

Figure 2A:
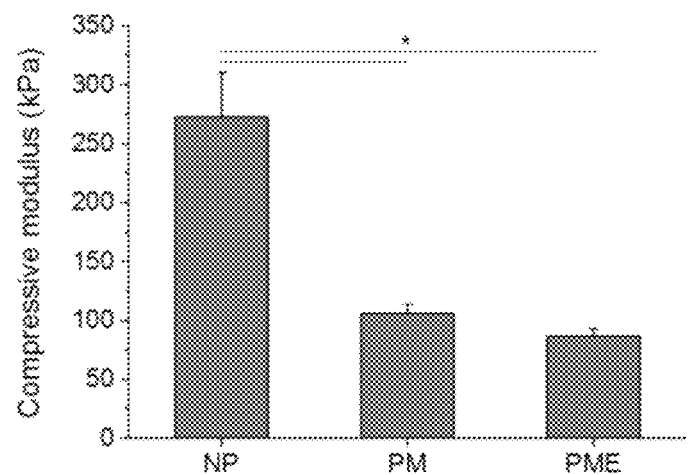
FIG. 2A is a graph providing the compressive modulus of hydrogels.
Figure 2B:
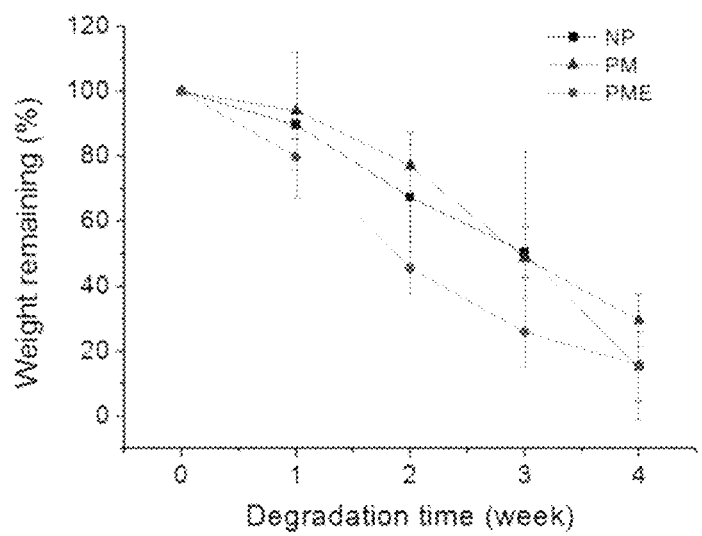
FIG. 2B is a graph showing hydrogel degradation profile of hydrogels. *Significant difference, $p<0.05$.

Physical properties of porous hydrogel: The compression modulus of the nonporous hydrogel (NP group) was 272±38 kPa. Pore structures significantly decreased the compression modulus to 106±8 kPa and 87±6 kPa for PM group and PME group, respectively (FIG. 2A). There was no difference in terms of degradation rate, hydrogel of PME group lost weight in PBS faster than NP and PM groups. As shown in FIG. 2B, PME hydrogel lost 50% weight in 2 weeks in collagenase/PBS, while similar weight loss took 3 weeks for the other two groups.

Figure 3:
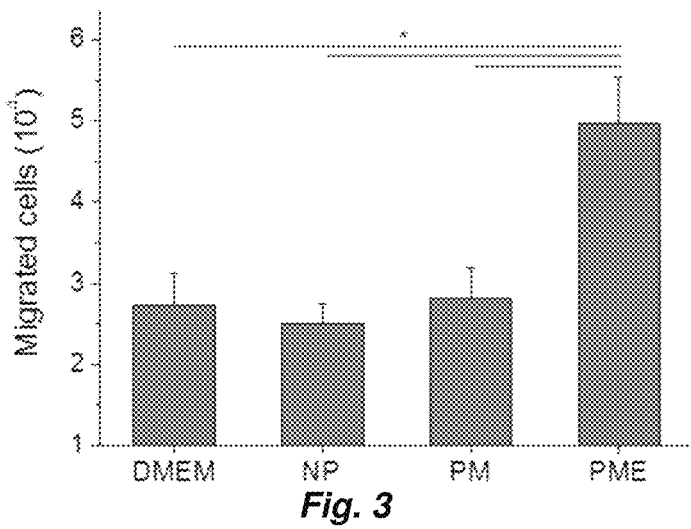
FIG. 3 is a graph showing chemotactic migration of macrophage induced by release products from hydrogels.

Influence of hydrogel on cell behaviors: Dissolved mannitol did not show cytotoxicity on SMCs up to 100 mM. Compared to SMCs treated with PBS, SMCs treated with products released from the hydrogels did not impact proliferation over a week. SMCs significantly proliferated during the culture period, as indicated by mitochondrial activity assay and visual inspection, but neither mannitol, proteins, MBVs nor other components promoted or inhibited cell proliferation over this period. On the other hand, the released products from the PME hydrogel attracted macrophages to migrate through 8 µm membrane towards the high concentration source, as shown in FIG. 3. Released products from the other two groups did not show a significant effect on macrophage migration compared to the PBS group (FIG. 3).

Figure 4:
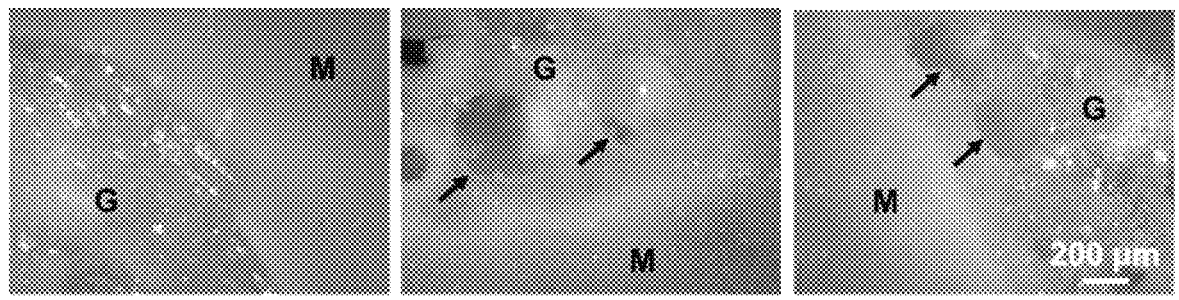
FIG. 4 are photomicrographs showing in situ pore formation in hydrogels after intramuscular injections. M: muscle, G: hydrogel, Arrows: boundary of pores.

Cell infiltration into hydrogel in vivo: Immediately after injection into the rat hindlimb, hydrogel from all three groups solidified and formed a hydrogel mass in the muscle bed as a result of temperature increase. As shown in FIG. 4, clear boundaries could be identified between the hydrogels and the muscle. For the hydrogel from the NP group, hydrogel mass was continuous and homogeneous, whereas pores can be found in injected PM and PME hydrogels (pointed by arrows in FIG. 4). In addition, similar to the in vitro result, channels between pores could be found in the PM and PME hydrogels.

Three days after injection, rat leg muscles with injected hydrogel were sectioned and stained. On DAPI stained images, hydrogel injection sites could be identified in all three groups. In NP and PM groups, empty regions were apparent on the tissue sections that were devoid of cell nuclei, corresponding to the region in which the hydrogels had been injected. These regions were encompassed by a capsule ~100 µm thick of densely packed cells (FIGS. 5A-5F). A similar capsule of cells was found around the injected hydrogel in the PME group. However, in contrast to the other two groups, cells were present in the hydrogel area, at a lower density compared to the cell density in the capsule. Of note, the entire hydrogel injection site was not infiltrated by cells. Rather, the core of the PME hydrogels remained cell-free 3 d after injection. As for the NPE group (non-porous VP10 hydrogel mixed with UBM digest), cells were observed to be further in the hydrogel from the hydrogel/capsule edge. However, the cells did not penetrate as far as in the PME group.

Figure 5A:
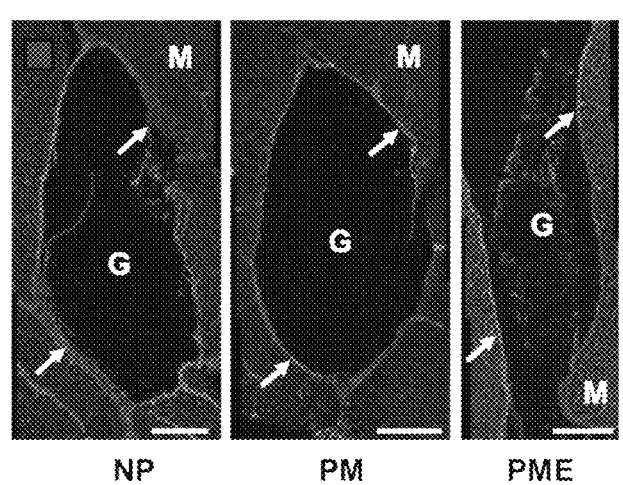
FIGS. 5A-5F. Cell infiltration into injected hydrogels. M: muscle, G: hydrogel, Arrows: foreign body capsule.
Figure 5B:
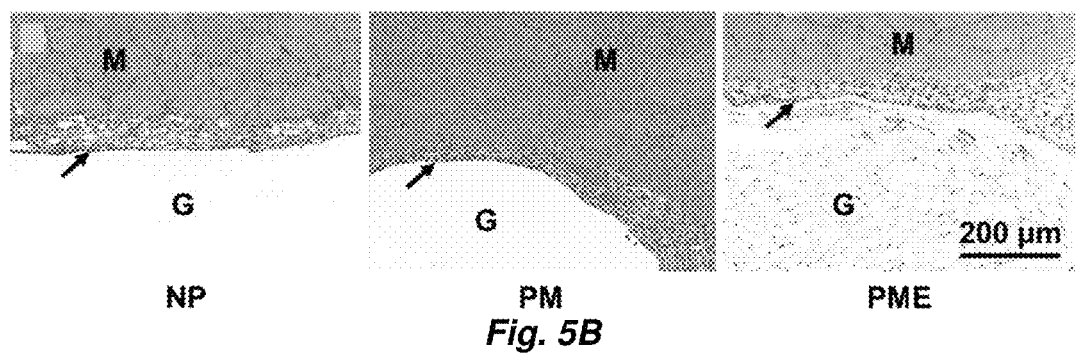
Figure 5C:
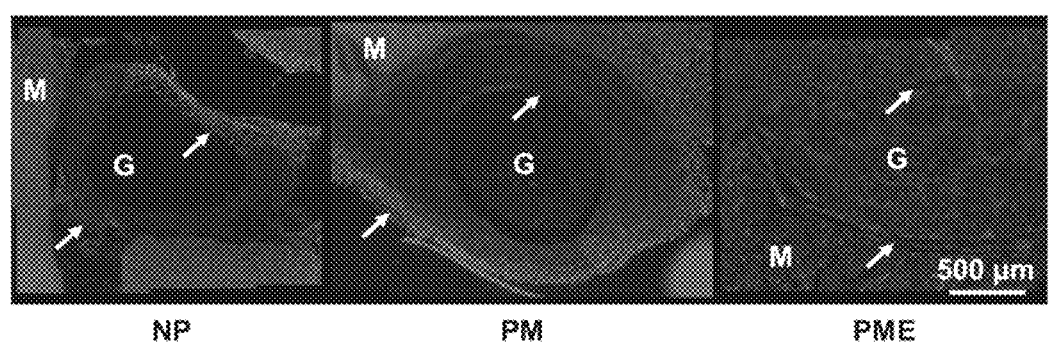
Figure 5D:
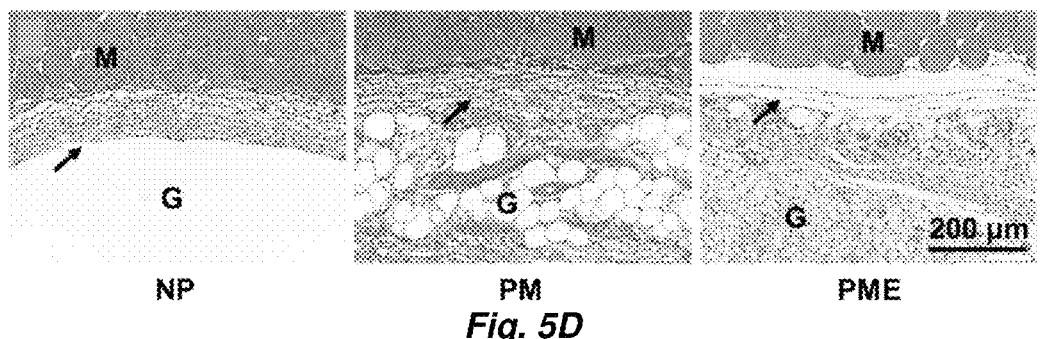
Figure 5E:
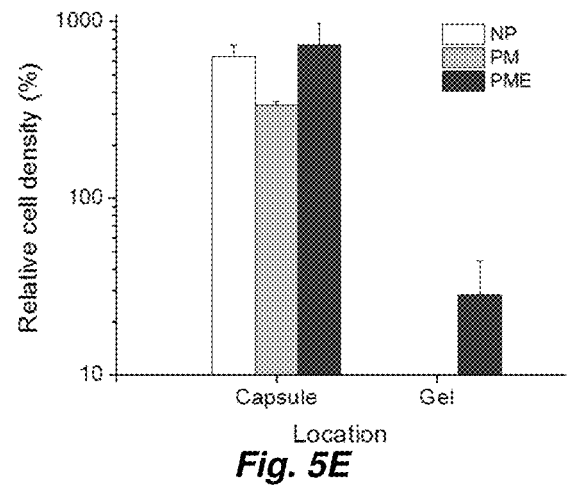
Figure 5F:
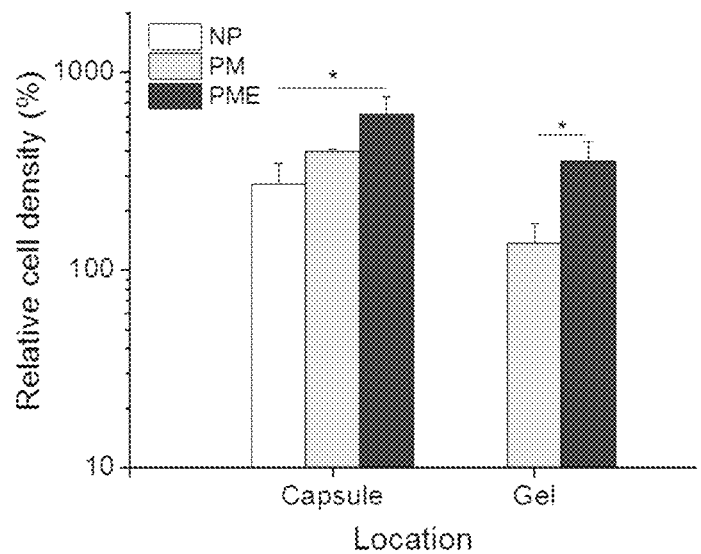

Twenty-one days after injection, the capsules surrounding the injection sites for all three groups did not show obvious changes regarding thickness or cell density compared to the capsules at day 3, as shown in FIG. 5C. For the two groups that did not show cell infiltration at day 3, no signs of cell infiltration in the NP group appeared given another 18 days, as opposed to the extensive infiltration towards the core of the injected hydrogel observed in the PM group. Similar to the NP group at day 3, the core of the PM hydrogel was not occupied by cells at day 21 (FIG. 5C). On the other hand, the entire injection site of the PME group was filled with cells, including the core of the hydrogel. As shown in FIG. 5C, the cells evenly distributed in the injection area, and the density of the infiltrated cells was significantly higher than the density of cells in the hydrogel area of the PM group. In addition, compared to day 3, the cell density in the injection area of the PME group at day 21 increased (FIG. 5F). Echoing the cell infiltration results, no extracellular matrix deposition was visually apparent at day 21 in the NP hydrogel injection area, while extensive extracellular matrix deposition was seen in sections from the PM and PME groups (FIG. 5D).

Figure 6A:
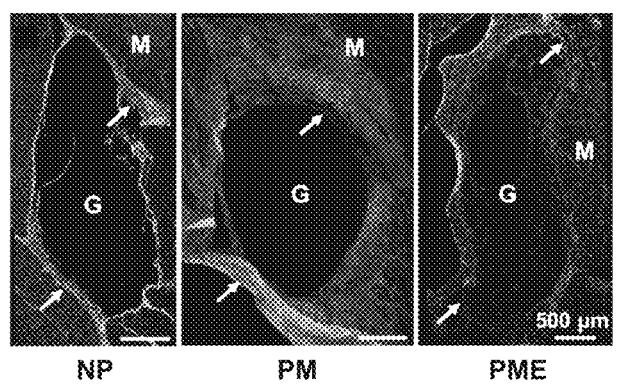
FIGS. 6A-6G. Macrophage polarization 3 days after hydrogel injection. M: muscle, G: hydrogel, Arrows: foreign body capsule.
Figure 6B:
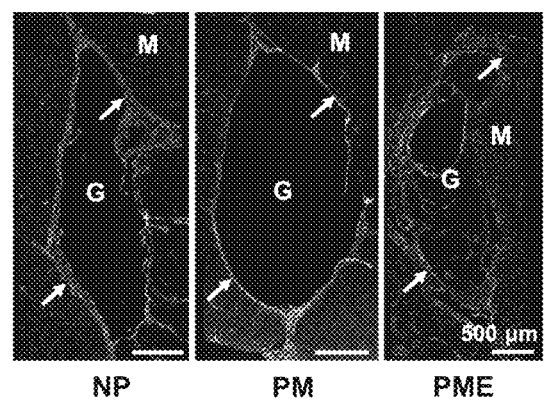
Figure 6C:
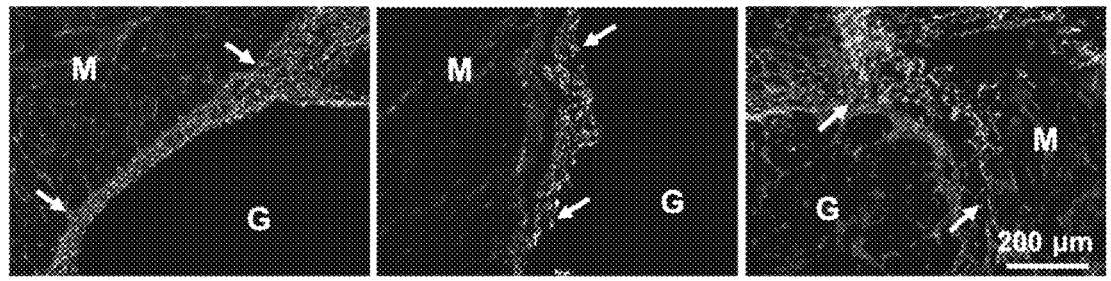
Figure 6D:
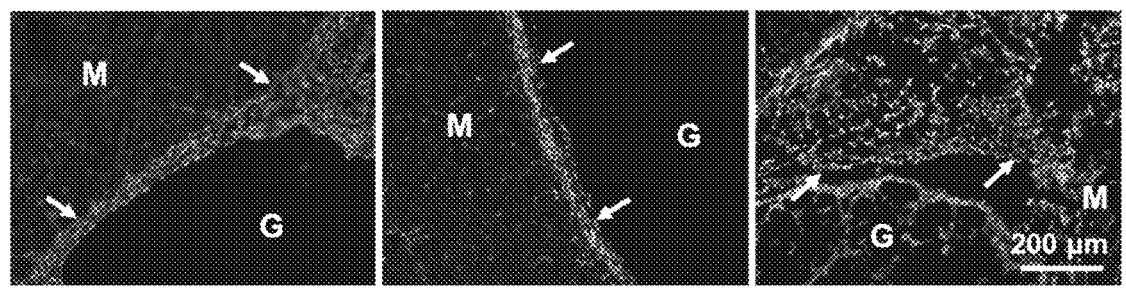
Figure 6E:
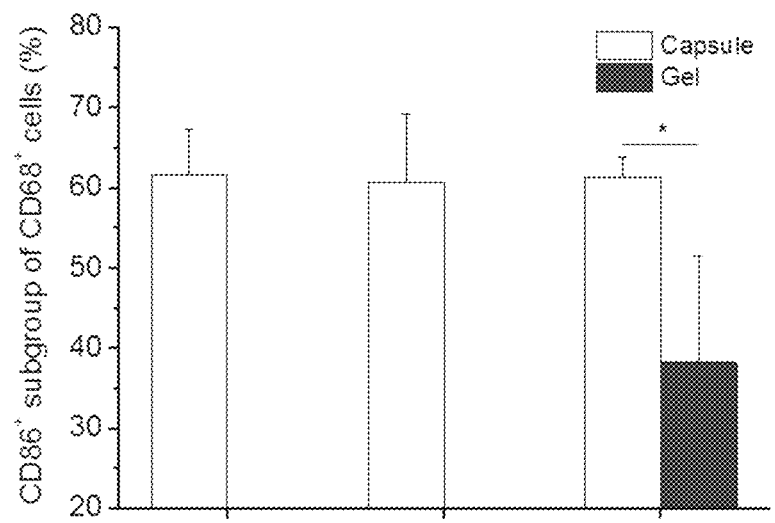
Figure 6F:
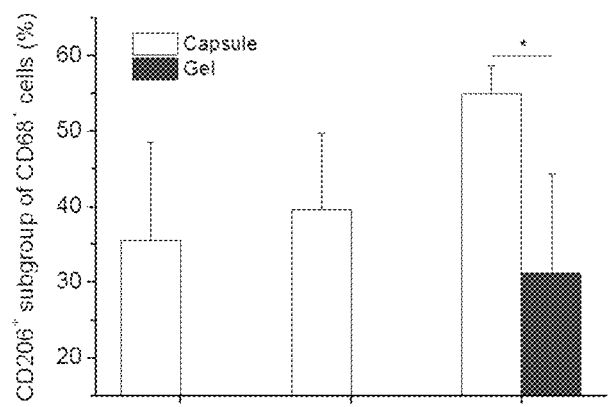
Figure 6G:
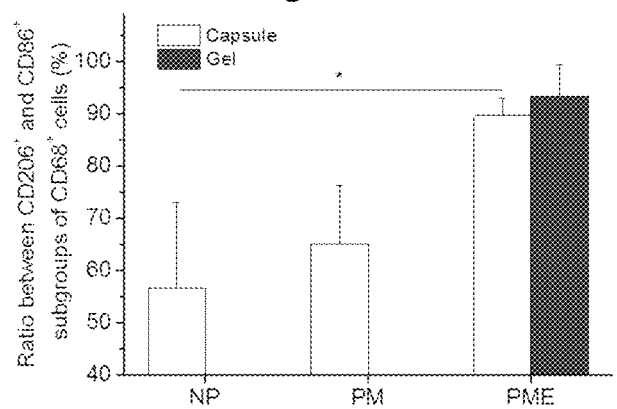

Macrophage polarization: Cells around and in the injection areas stained positively with macrophage markers. CD68 (red)/CD86 (green) and CD68 (red)/CD206 (green) were stained on separate sections. As shown in FIGS. 6A-6D, CD68$^+$ cells were present in, concentrated in and comprised the major portion of the cell population in the capsule around the injection areas for all three groups at day 3. Colocalization of the red fluorescence from CD68 and green fluorescence from CD86 was observed in all three groups, resulting in yellow cells in the capsules (FIGS. 6A and 6C). The CD68$^+$/CD86$^+$ subgroups of macrophages (CD68$^+$ cells) were evenly distributed in the capsules without preference on either the hydrogel side or the muscle side. Quantitative results given by CellProfiler showed that around 60% of the macrophages were CD86 positive for all three groups at day 3 (FIG. 6E). CD68$^+$/CD206$^+$ subgroups of macrophages were also identified in the capsules (FIGS. 6B and 6D). Similar to the CD86$^+$ macrophages, CD206$^+$ macrophages distributed evenly in the capsules. For NP, PM, and PME, 35%, 40% and 55% of the macrophages were CD206+, respectively (FIG. 6F). However, no significant differences among the CD206+ percentages were identified. Further calculation showed that the ratio between CD206+ macrophages and CD86+ macrophages for the NP group (57%) was smaller than for the PME group (90%) group (FIG. 6G), indicating that the macrophages in the capsules around injected NP hydrogel were polarized more toward an M1 phenotype compared to the PME group. No differences were found between the NP and PM groups, or between PM and PME groups. Since no cells had infiltrated the NP and PM hydrogels at day 3, only the infiltrating macrophage polarization for the PME group was analyzed. Compared to macrophages in the capsule, macrophages in the PME hydrogel were less polarized, as both the CD86+ and CD206+ percentages were smaller (FIGS. 6E and 6F). However, the ratio between CD206+ macrophages and CD86+ macrophages was not different from the ratio of the macrophages in the capsule (FIG. 6G).

Figure 7A:
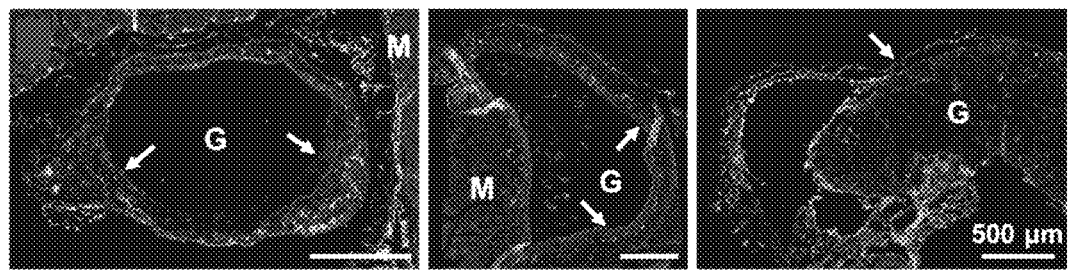
FIGS. 7A and 7B. Macrophage polarization in hydrogel injection sites after 21 days. M: muscle, G: hydrogel, Arrows: foreign body capsule.
Figure 7B:
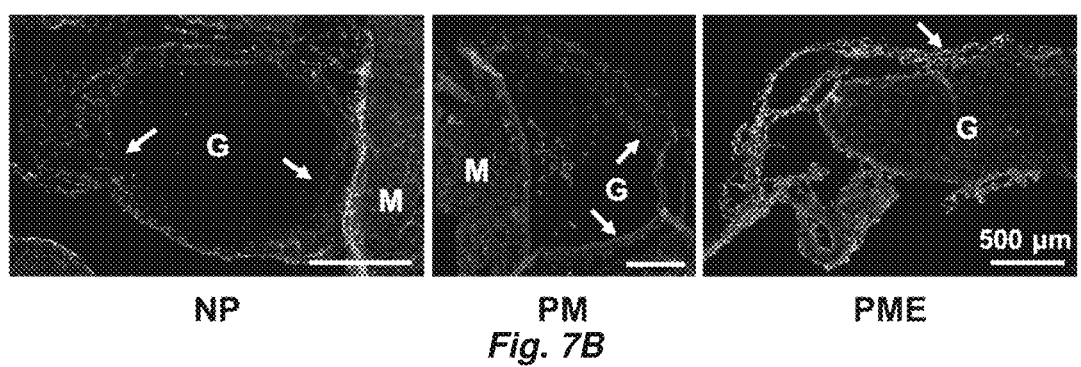
Figure 7C:
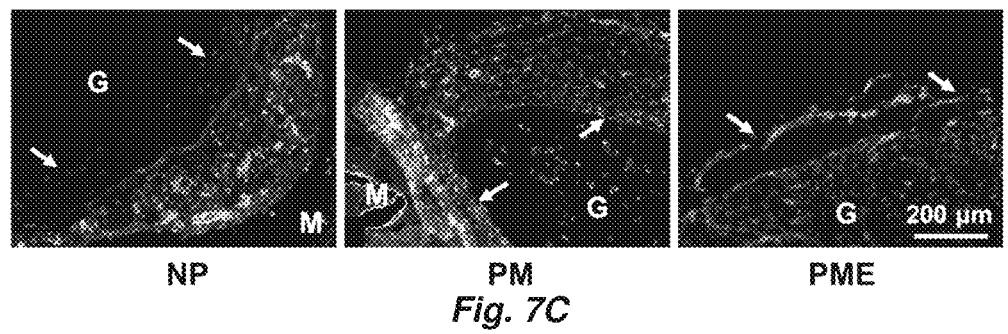
FIG. 7C CD86 (green in original) and CD68 (red in original) and FIG. 7D CD206 (green in original) and CD68 (red in original) staining at the hydrogel/muscle interface.
Figure 7D:
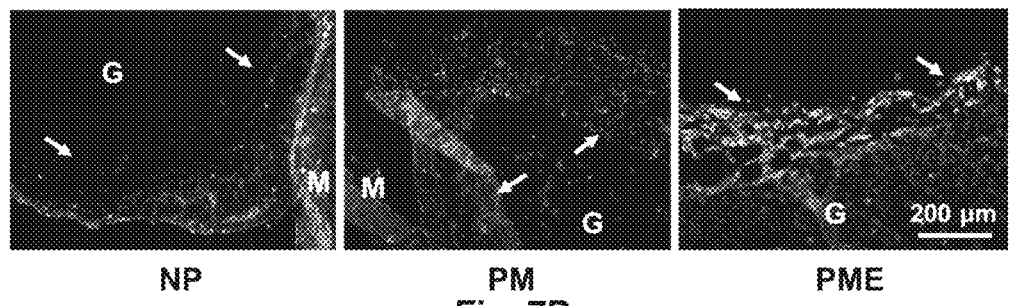
FIGS. 7E and 7F. Percentage of $CD86^+$ and $CD206^+$ cells in $CD68^+$ population, respectively.
FIG. 7G. Ratio between $CD86^+$ and $CD206^+$ cells in $CD68^+$ population. *Higher than PM group, #Higher than NP and PM groups, $p<0.05$.
Figure 7E:
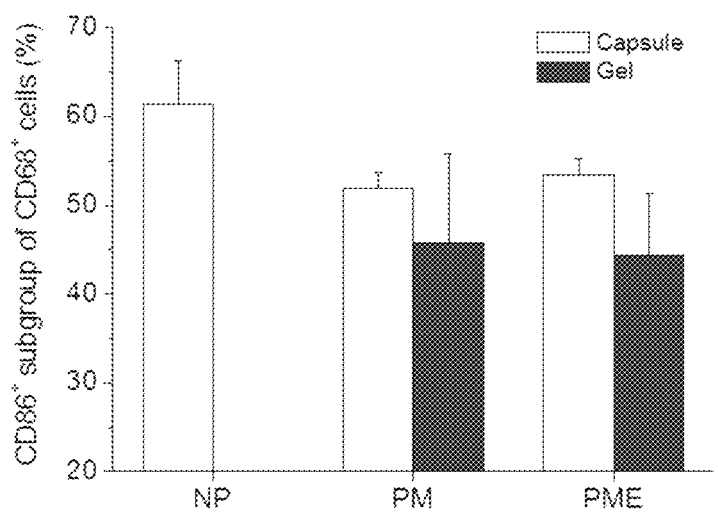
Figure 7F:
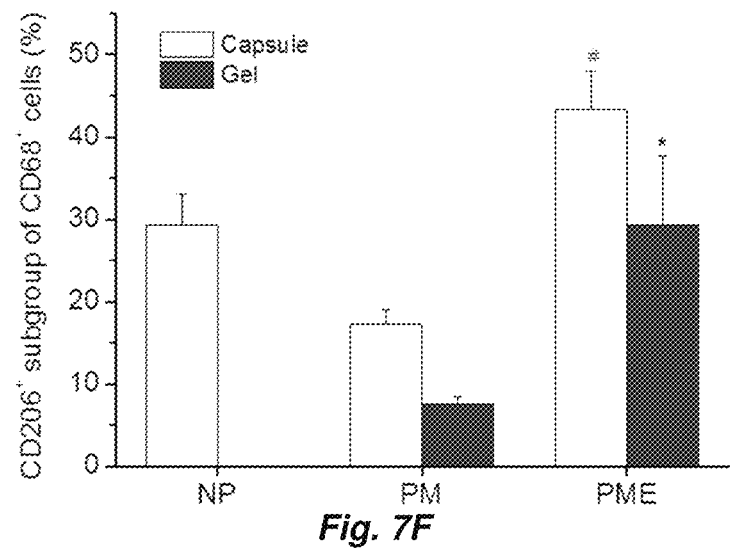
Figure 7G:
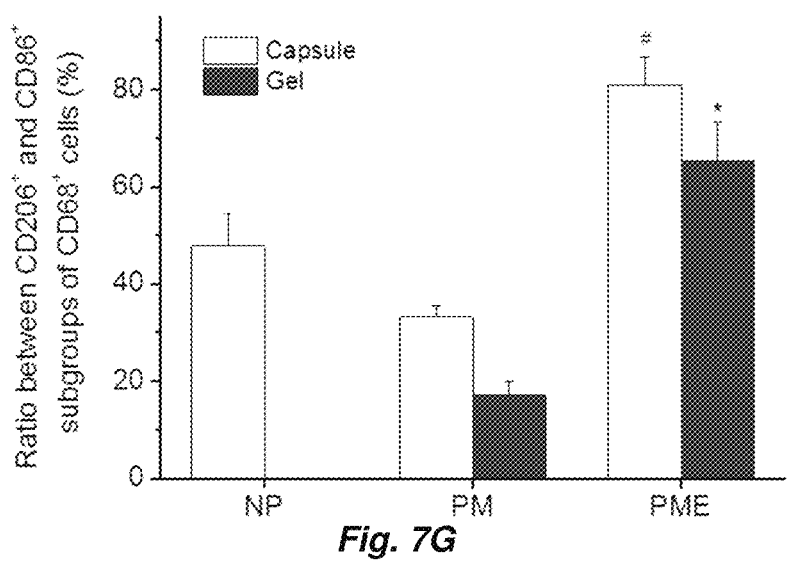

At day 21, the foreign body response did not diminish, with macrophages remaining around and within the injection sites, as shown in FIGS. 7A and 7B. CD68 staining showed cells infiltrating the PM hydrogel and that the cells following the first wave of infiltration in the PME hydrogel were mostly macrophages (FIGS. 7A and 7B). Similar to the results at day 3, colocalization of CD68 and CD86 was observed for a significant portion of the macrophages in the capsules for all three groups (FIGS. 7A and 7C). The percentage of CD86+ macrophages decreased significantly between day 3 (61%) and day 21 (53%) for the PME group, while the percentages did not change significantly for NP and PM groups (FIG. 7E). In terms of the CD206+ subgroup of macrophages in the capsules, the percentages decreased significantly between day 3 (40% and 55%) and day 21 (17% and 43%) for PM and PME groups respectively, while no significant changes were found for the NP group (FIG. 7F). From day 3 to day 21, the ratio between CD206+ macrophages and CD86+ macrophages in the capsules for the PM group decreased significantly, while the ratios for the NP and PME groups remained at the same level (FIG. 7F). As a result, the PME group showed the highest CD206+/CD86+ ratio among the three groups, and the ratio for the NP group was higher than for the PM group. In terms of the CD206+/CD86+ ratio, the macrophages infiltrating the PM hydrogel appeared to be more polarized toward the M1 phenotype compared to the macrophages in the capsule around the PM hydrogel and the macrophages infiltrating the PME hydrogel (FIG. 7G).

Figure 8:
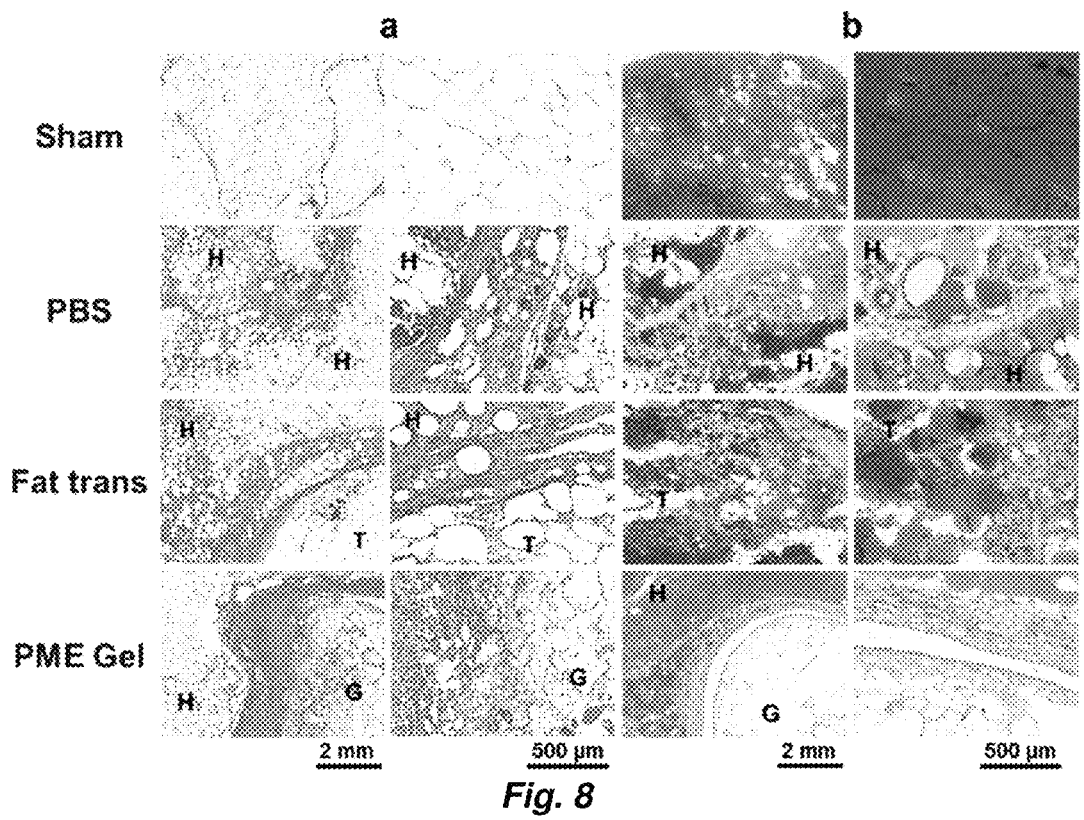
FIG. 8. Morphology of rabbit adipose tissue 2 weeks after treatment. H: healthy tissue, T: transplant. (a) Trichrome staining. (b) Oil Red staining.

Repair of adipose tissue defect: Two weeks after surgery, adipose tissue samples collected from rabbits in the Sham group showed structures resembling that of healthy adipose tissue, featuring densely packed hexagonal adipocytes (FIG. 8(a)). In contrast, for the PBS injection group, the defect wounds closed and were infiltrated by scar tissue. Inflammation could be found in adipose tissue adjacent to the scar: the organized structure of adipocytes was disrupted by inflammatory cell infiltration and collagen deposition. Similar to the PBS group, inflammation was observed in and around transplanted autologous fat, especially along the boundary of the tissue bed and the implanted tissue. In comparison, adipose tissue near the defect filled with PME hydrogel maintained the morphology of healthy fat tissue. A thick layer of cells attributed to the foreign body response encompassed the injected PME hydrogel, comparable to the phenomenon found in the rat model (hydrogel mass could be observed during the excision procedure). As shown in FIG. 8, there was extensive cellular penetration across the hydrogel-tissue interface and infiltrating the porous hydrogel, consistent with previous findings, yet at this time point there was not morphological evidence of new adipose tissue in the hydrogel pocket. Oil Red staining supported the observations made from the trichrome staining. Oil droplets occupied almost all of the volume in the adipocytes and the volume of the adipose tissue. This characteristic of normal adipose tissue was also present in fat tissue around the implanted hydrogel. In contrast, oil droplets in the PBS group and Fat Transplantation group lost their normal morphology, with smaller, disjointed areas staining positively with Oil Red. These stained areas were discontinuous compared to those in the Sham and PME Gel groups.

Figure 9:
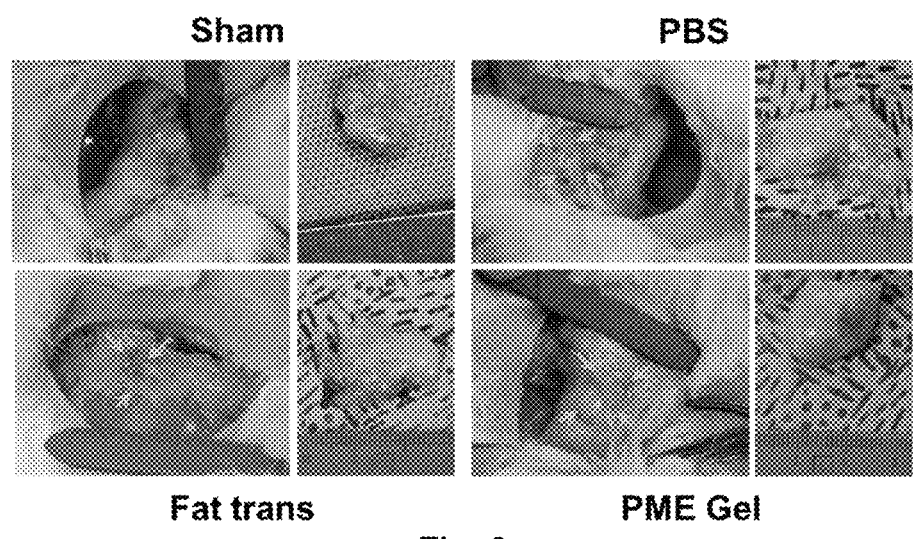
FIG. 9. Gross appearance of rabbit adipose tissue 8 weeks after treatment. Arrows: suture markers.
Figure 10:
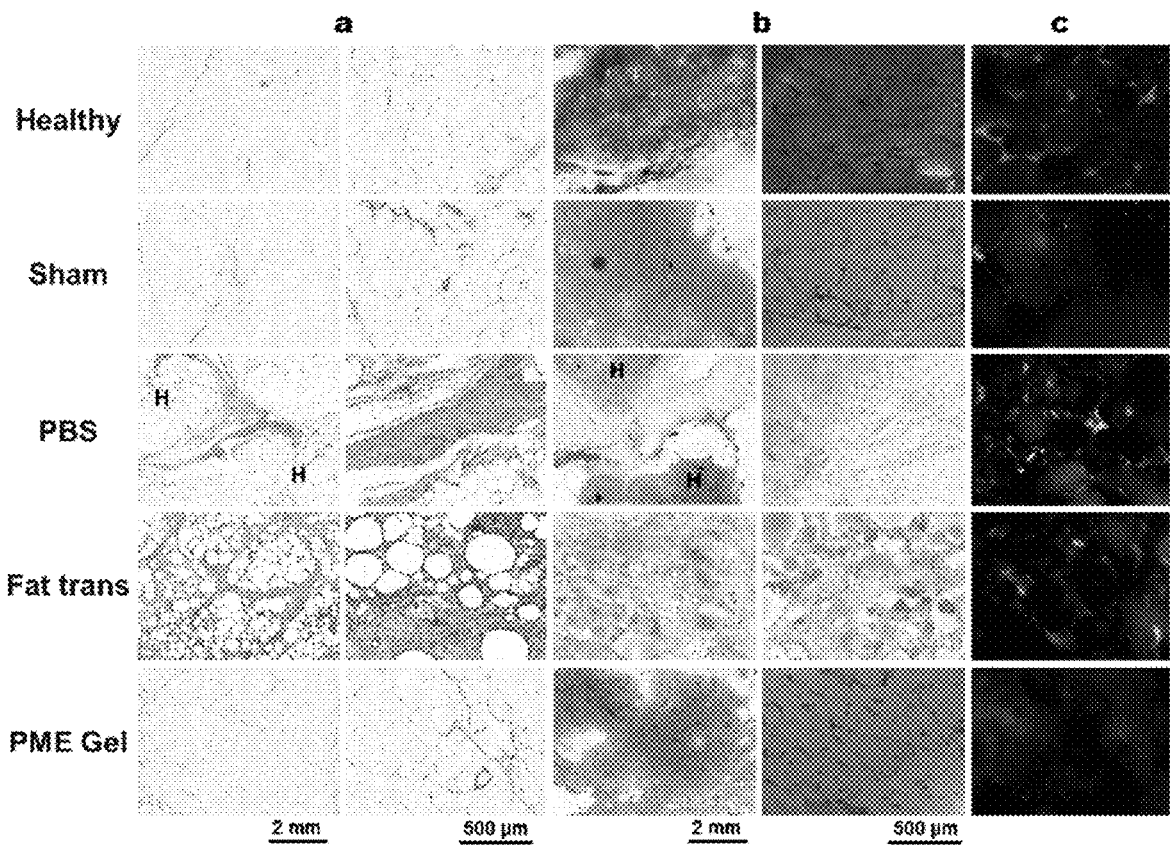
FIG. 10. Morphology of rabbit adipose tissue 8 weeks after treatment. H: healthy tissue. (a) Trichrome staining. (b)

At 8 weeks post-surgery, the gross appearance of the treated adipose tissue in the animals is shown in FIG. 9. Unlike the 2 week time point, no hydrogel mass was found in the PME hydrogel treated group. Despite migration and tissue encapsulation, more than half of the suture markers could be located after 8 weeks and were generally found to have maintained the square layout created at the time of intervention (FIG. 9). The distances between the markers in the PBS group appeared to have decreased as the defects closed, whereas the marker patterns in the Fat Transplantation group and PME Hydrogel group did not appear to shrink. Due to the loss of some of the markers and the limited numbers of rabbits in each group, this observation was necessarily qualitative. Tactile semi-quantitative evaluation of the treated areas prior to re-opening of the surgical site revealed that the tissue for the Fat Transplantation group, but not the other groups, became stiffer (stiffness score increased from 1.8±0.3 to 2.8±0.3 in the Fat Transplantation group). Further qualitative examination of the tissue surrounding the surgical areas indicated that these tissues did not stiffen for any of the groups. The stiffening of the fat transplanted site was consistent with the extensive chronic inflammation and fibrotic tissue deposition found histologically in the Fat Transplantation group (FIG. 10). Mild inflammation was observed near the scar formed in the defect of the PBS group, which appeared to have dissipated from the acute inflammation found at 2 weeks post-surgery. Tissue collected from the Sham and PME Gel groups exhibited little morphological differences compared to the healthy control tissue, showing negligible signs of inflammation or fibrosis (FIG. 10). Oil Red staining reflected the observations made with trichrome staining. The organization of adipocytes in the Sham, PME Gel, and PBS groups (besides the scar tissue apparent in the latter group) resembled that of the Healthy group, while adipocytes in the Fat Transplantation group were interspersed with fibrotic tissue. Isolectin staining (red channel in the right column of FIG. 10) highlighted vascular structures and macrophages within the treated adipose tissue. PME Gel treated adipose tissue generally presented a vascular morphology similar to that of the Sham and Healthy groups. Putative macrophages were apparent in sites treated with the transplanted fat tissue, co-localizing with fibrotic tissue and making it difficult to discern the vasculature. A high density of macrophages was also found in the scar and at the interface of the scar and healthy adipose tissue in tissues in the PBS group.

Adipocyte size is a reflection of the status of the cells, which is influenced by metabolic activities, inflammation, and fibrosis of the adipose tissue. In terms of cell area in tissue cross-section, the adipocyte size distribution for healthy fat presented a single peak distribution, with the most frequent area being between 4000 and 5000 $\mu m^2$ (FIGS. 11A-11C). For the Sham group 8 weeks after surgery, a subpopulation of the adipocytes became larger, with the primary peak area being comparable to healthy tissue. For the three types of treated defects, the peaks of the area distribution shifted smaller with each showing the highest frequency between 1000 and 2000 µm². The size distribution for the PBS group showed a single, narrow peak, while the distribution for the PME Gel group was skewed with a tail of larger adipocytes. Distinct from other groups, the adipocyte area distribution for the Fat Transplantation group had a longer tail in the larger area region; a significant subgroup of the adipocytes being larger than 15000 µm². On average, adipocytes in the Fat Transplantation group were larger than for all other groups (FIG. 11B), whereas the cells were smaller in the PBS treated tissue. Adipocytes from the PME Gel treated tissue had a similar average area compared to the Healthy and Sham groups. Looking at another morphological parameter, the number of crown-like structures were quantified for all groups. This parameter, related to apoptotic activity, was found to be markedly elevated for the Fat Transplantation group.

The following numbered clauses describe various exemplary aspects of the invention.

Clause 1. A composition comprising: a biodegradable, biocompatible, gelling polymer composition; ECM material; and a biocompatible porogen that dissolves in vivo within 48 hours, or optionally within 24 hours, and wherein the composition forms a gel at 37° C. within one hour, 30 minutes, 15 minutes, five minutes, or two minutes.

Clause 2. The composition of clause 1, wherein the composition forms a gel in vivo within ten minutes, five minutes, or two minutes.

Clause 3. The composition of clause 1, wherein the biodegradable, biocompatible, polymer composition is reverse-gelling.

Clause 4. The composition of any one of clauses 1-3, comprising: from 10% to 94.9% of a biodegradable, biocompatible, gelling polymer composition; from 0.1% to 50% of solubilized ECM material; and from 5% to 65% of the biocompatible porogen.

Clause 5. The composition of any one of clauses 1-4, wherein the biodegradable, biocompatible, gelling polymer composition comprises a poly(NIPAAm-co-VP-co-MAPLA) polymer composition.

Clause 6. The composition of clause 5, wherein the composition feed ratio or relative amounts of monomer residues for the poly(NIPAAm-co-VP-co-MAPLA) polymer is NIPAAm 60%-90%, VP+MAPLA 40%-10%.

Clause 7. The composition of any one of clauses 1-6, wherein the ECM material is solubilized by digestion with an acid protease at pH 1 to 4.

Clause 8. The composition of clause 7, wherein the acid-protease digested ECM material is reverse-gelling.

Clause 9. The composition of any one of clauses 1-8, wherein the porogen particles have a size or average size of between 30 µm and 300 µm.

Clause 10. The composition of any one of clauses 1-9, wherein the porogen dissolves in vivo after gelation of the composition, and within 48 hours of gelation, or within 24 hours of gelation.

Clause 11. The composition of any one of clauses 1-9, wherein the porogen is a salt, sugar, polysaccharide, protein, or polypeptide.

Clause 12. The composition of any one of clauses 1-9, wherein the porogen is mannitol.

Clause 13. A method of making a composition for use in tissue repair, comprising: mixing a biodegradable, biocompatible, gelling polymer composition with a comminuted or solubilized ECM material, and a biocompatible porogen that dissolves in vivo within 48 hours, or optionally 24 hours, wherein the composition forms a gel at 37° C. within one hour, 30 minutes, 15 minutes, five minutes, or two minutes.

Clause 14. The method of clause 13, wherein the composition forms a gel at in vivo within ten minutes, five minutes, or two minutes.

Clause 15. The method of clause 13, wherein the biodegradable, biocompatible, polymer composition is reverse-gelling.

Clause 16. The method of any one of clauses 13-15, comprising: from 10% to 94.9% of a biodegradable, biocompatible, gelling polymer composition; from 0.1% to 50% of solubilized ECM material; and from 5% to 65% of the biocompatible porogen.

Clause 17. The method of clause 16, wherein the biodegradable, biocompatible, reverse-gelling polymer composition comprises a poly(NIPAAm-co-VP-co-MAPLA) polymer composition.

Clause 18. The method of clause 17, wherein the composition feed ratio or relative amounts of monomer residues for the poly(NIPAAm-co-VP-co-MAPLA) polymer is NIPAAm 60%-90%, VP+MAPLA 40%-10%.

Clause 19. The method of any one of clauses 13-18, wherein the ECM material is solubilized by digestion with an acid protease at pH 1 to 4.

Clause 20. The method of clause 19, wherein the acid-protease digested ECM material is reverse-gelling.

Clause 21. The method of any one of clauses 13-20, wherein the porogen particles have a size or average size of between 30 µm and 300 µm.

Clause 22. The method of any one of clauses 13-21, wherein the porogen dissolves in vivo after gelation of the composition, and within 48 hours of gelation, or within 24 hours of gelation.

Clause 23. The method of any one of clauses 13-21, wherein the porogen is a salt, sugar, polysaccharide, protein, or polypeptide.

Clause 24. The method of any one of clauses 13-21, wherein the porogen is mannitol.

Clause 25. The method of any one of clauses 13-24, wherein the porogen is added to a mixture of the polymer composition and the comminuted or solubilized ECM material at a time after the time when the polymer composition and the comminuted or solubilized ECM material are mixed.

Clause 26. The method of any one of clause 13-24, wherein one or more of the polymer composition and the comminuted or solubilized ECM material is lyophilized and re-hydrated, or frozen and thawed prior to mixing.

Clause 27. The method of any one of clauses 13-24, further comprising lyophilizing or freezing the composition after mixing.

Clause 28. A method of treating a defect or wound in a patient, comprising administering to the patient at or adjacent to the site of the wound or defect in the patient, an amount of the composition of any one of clauses 1-12 effective to treat or repair the wound or defect in a patient.

Clause 29. The method of clause 28, wherein the defect or wound is a soft tissue defect or wound.

Clause 30. A kit comprising one or more vessels containing: a biodegradable, biocompatible, gelling polymer composition; comminuted or solubilized ECM material; and a biocompatible porogen that dissolves in vivo within 48 hours, or optionally 24 hours, wherein the polymer composition, the comminuted or solubilized ECM material, and the porogen are contained together or in separate vessels in a liquid, frozen, dried, or lyophilized state.

Clause 31. The kit of clause 30, wherein the polymer composition and the comminuted or solubilized ECM material are provided in a single vessel in liquid, frozen, or lyophilized state, and the porogen particles are provided in a separate vessel.

Clause 32. The kit of clause 30 or 31, wherein the polymer composition, the comminuted or solubilized ECM material, and the porogen, when mixed in an aqueous solution forms a gel at 37° C. within one hour, 30 minutes, 15 minutes, five minutes, or two minutes.

Clause 33. The kit of any one of clauses 30-32, wherein the biodegradable, biocompatible, polymer composition is reverse-gelling.

Clause 34. The kit of any one of clauses 30-33, comprising: from 10% to 94.9% of a biodegradable, biocompatible, gelling polymer composition; from 0.1% to 50% of solubilized ECM material; and from 5% to 65% of the biocompatible porogen.

Clause 35. The kit of any one of clauses 30-34, wherein the biodegradable, biocompatible, gelling polymer composition comprises a poly(NIPAAm-co-VP-co-MAPLA) polymer composition.

Clause 36. The kit of clause 35, wherein the composition feed ratio or relative amounts of monomer residues for the poly(NIPAAm-co-VP-co-MAPLA) polymer is NIPAAm 60%-90%, VP+MAPLA 40%-10%.

Clause 37. The kit of any one of clauses 30-36, wherein the ECM material is solubilized by digestion with an acid protease at pH 1 to 4.

Clause 38. The kit of clause 37, wherein the acid-protease digested ECM material is reverse-gelling.

Clause 39. The kit of any one of clauses 30-38, wherein the porogen particles have a size or average size of between 30 µm and 300 µm.

Clause 40. The kit of any one of clauses 30-39, wherein the porogen dissolves in vivo after gelation of the composition, and within 48 hours of gelation, or within 24 hours of gelation.

Clause 41. The kit of any one of clauses 30-40, wherein the porogen is a salt, sugar, polysaccharide, protein, or polypeptide.

Clause 42. The kit of any one of clauses 30-41, wherein the porogen is mannitol.

Clause 43. The kit of any one of clauses 30-42, wherein the polymer composition, the comminuted or solubilized ECM material, and the porogen are contained together and are lyophilized.

The present invention has been described in accordance with several examples, which are intended to be illustrative in all aspects rather than restrictive. Thus, the present invention is capable of many variations in detailed implementation, which may be derived from the description contained herein by a person of ordinary skill in the art.

We claim:

1. A composition comprising:
   10% to 94.9% by weight of the composition of a biodegradable, biocompatible, gelling poly(NIPAAm-co-VP-co-MAPLA) polymer composition, that is reverse-gelling;
   an aqueous solvent;
   0.1% to 50% by weight of the composition of extracellular matrix (ECM) material, wherein the ECM material is solubilized by digestion with an acid protease at pH 1 to 4, and wherein the acid-protease digested ECM material is reverse-gelling; and
   5% to 65% by weight of the composition of a biocompatible porogen that dissolves in vivo within 48 hours, wherein the biocompatible porogen comprises mannitol,
   wherein the composition forms a gel at 37° C. within one hour, 30 minutes, 15 minutes, five minutes, or two minutes.

2. The composition of claim 1, wherein the composition forms a gel in vivo within ten minutes, five minutes, or two minutes.

3. The composition of claim 1, wherein the composition feed ratio or relative amounts of monomer residues for the poly(NIPAAm-co-VP-co-MAPLA) polymer is NIPAAm 60%-90%, VP+MAPLA 40%-10%.

4. The composition of claim 1, wherein the porogen particles have a size or average size of between 30 µm and 300 µm.

5. A method of making a composition for use in tissue repair, comprising: mixing 10% to 94% by weight of the composition of a biodegradable, biocompatible, gelling poly(NIPAAm-co-VP-co-MAPLA) polymer composition, that is reverse-gelling, with an aqueous solvent, 0.1% to 50% by weight of the composition of an ECM material, wherein the ECM material is solubilized by digestion with an acid protease at pH 1 to 4, and wherein the acid-protease digested ECM material is reverse-gelling, and 5% to 65% by weight of the composition of a biocompatible porogen that dissolves in vivo within 48 hours, wherein the biocompatible porogen comprises mannitol, wherein the composition forms a gel at 37° C. within one hour, 30 minutes, 15 minutes, five minutes, or two minutes, wherein the composition forms a gel in vivo within ten minutes, five minutes, or two minutes, and optionally wherein the porogen particles have a size or average size of between 30 µm and 300 µm.

6. The method of claim 5, wherein the composition feed ratio or relative amounts of monomer residues for the poly(NIPAAm-co-VP-co-MAPLA) polymer is NIPAAm 60%-90%, VP+MAPLA 40%-10%.

7. The method of claim 5, wherein the porogen is added to a mixture of the polymer composition and the comminuted or solubilized ECM material at a time after the time when the polymer composition and the comminuted or solubilized ECM material are mixed; wherein one or more of the polymer composition and the comminuted or solubilized ECM material is lyophilized and re-hydrated, or frozen and thawed prior to mixing; and/or further comprising lyophilizing or freezing the composition after mixing.

8. A method of treating a defect or wound in a patient, comprising administering to the patient at or adjacent to the site of the wound or defect in the patient, an amount of the composition of claim 1 effective to treat or repair the wound or defect in a patient, wherein the defect or wound optionally is a soft tissue defect or wound.

9. A kit comprising one or more vessels containing:
   10% to 94.9% by weight of a biodegradable, biocompatible, gelling poly(NIPAAm-co-VP-co-MAPLA) polymer composition;
   an aqueous solvent;
   0.1% to 50% by weight of ECM material, wherein the ECM material is solubilized by digestion with an acid protease at pH 1 to 4; and
   5% to 65% by weight of a biocompatible porogen that dissolves in vivo within 48 hours,
   wherein the polymer composition, the ECM material, and the porogen are contained together or in separate vessels in a liquid, frozen, dried, or lyophilized state, and wherein the biocompatible porogen comprises mannitol.

10. The kit of claim 9, wherein the polymer composition and the ECM material are provided in a single vessel in liquid, frozen, or lyophilized state, and the porogen particles are provided in a separate vessel.

11. The kit of claim 9, wherein the polymer composition, the ECM material, and the porogen, when mixed in an aqueous solution, forms a gel at 37° C. within one hour, 30 minutes, 15 minutes, five minutes, or two minutes.

12. The kit of claim 9, wherein
the porogen particles have a size or average size of between 30 μm and 300 μm.

13. The kit of claim 9, wherein the composition feed ratio or relative amounts of monomer residues for the poly (NIPAAm-co-VP-co-MAPLA) polymer is NIPAAm 60%-90%, VP+MAPLA 40%-10%.

14. The kit of claim 9, wherein the porogen dissolves in vivo after gelation of the composition, and within 48 hours of gelation, or within 24 hours of gelation.

* * * * *

UNITED STATES PATENT AND TRADEMARK OFFICE
CERTIFICATE OF CORRECTION

| | | |
|---|---|---|
| PATENT NO. | : 11,389,569 B2 | Page 1 of 1 |
| APPLICATION NO. | : 16/496480 | |
| DATED | : July 19, 2022 | |
| INVENTOR(S) | : Badylak et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 83 days.

Signed and Sealed this
Fourth Day of July, 2023

Katherine Kelly Vidal
*Director of the United States Patent and Trademark Office*